(12) United States Patent
Shenoy et al.

(10) Patent No.: US 9,821,041 B2
(45) Date of Patent: *Nov. 21, 2017

(54) CRYSTALLIZED OXALATE DECARBOXYLASE AND METHODS OF USE

(71) Applicant: Allena Pharmaceuticals, Inc., Newton, MA (US)

(72) Inventors: Bhami C. Shenoy, South Grafton, MA (US); Teresa G. Cachero, Hingham, MA (US); John Shin, Burlington, MA (US); Lekai Zhang, Watertown, MA (US); Aftab Rashid, Natick, MA (US); Danica Grujic, Boston, MA (US); Reena J. Patel, Woburn, MA (US); Margaret Ellen McGrath, Somerville, MA (US)

(73) Assignee: Allena Pharmaceuticals, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/843,751

(22) Filed: Sep. 2, 2015

(65) Prior Publication Data

US 2016/0051647 A1 Feb. 25, 2016

Related U.S. Application Data

(60) Division of application No. 14/283,794, filed on May 21, 2014, now Pat. No. 9,155,785, which is a continuation of application No. 13/372,274, filed on Feb. 13, 2012, now Pat. No. 8,741,284, which is a division of application No. 11/833,082, filed on Aug. 2, 2007, now Pat. No. 8,142,775.

(60) Provisional application No. 60/854,540, filed on Oct. 26, 2006, provisional application No. 60/834,933, filed on Aug. 2, 2006.

(51) Int. Cl.
| | |
|---|---|
| *A61K 38/00* | (2006.01) |
| *A61K 38/51* | (2006.01) |
| *C12N 9/88* | (2006.01) |
| *C12Q 1/527* | (2006.01) |
| *A61K 9/00* | (2006.01) |
| *A61M 1/16* | (2006.01) |
| *A61M 1/36* | (2006.01) |

(52) U.S. Cl.
CPC ............ *A61K 38/51* (2013.01); *A61K 9/0034* (2013.01); *A61M 1/16* (2013.01); *A61M 1/3687* (2013.01); *C12N 9/88* (2013.01); *C12Q 1/527* (2013.01); *A61K 38/00* (2013.01); *A61M 2202/0413* (2013.01); *A61M 2205/75* (2013.01); *C07K 2299/00* (2013.01); *C12Y 401/01002* (2013.01); *G01N 2333/988* (2013.01)

(58) Field of Classification Search
None
See application file for complete search history.

(56) References Cited

U.S. PATENT DOCUMENTS

| | | | |
|---|---|---|---|
| 5,866,778 | A | 2/1999 | Hartman et al. |
| 5,976,529 | A | 11/1999 | Navia et al. |
| 6,140,475 | A | 10/2000 | Margolin et al. |
| 6,218,134 | B1 | 4/2001 | Yamauchi et al. |
| 6,229,065 | B1 | 5/2001 | Freyssinet et al. |
| 6,235,530 | B1 | 5/2001 | Freyssinet et al. |
| 6,281,252 | B1 | 8/2001 | Holmes-Farley et al. |
| 6,503,507 | B1 | 1/2003 | Allen |
| 6,541,606 | B2 | 4/2003 | Margolin et al. |
| 6,929,940 | B1 | 8/2005 | Richards et al. |
| 8,142,775 | B2 | 3/2012 | Shenoy et al. |
| 8,741,284 | B2 | 6/2014 | Shenoy et al. |
| 9,155,785 | B2 | 10/2015 | Shenoy et al. |
| 2003/0113308 | A1 | 6/2003 | Sidhu |
| 2004/0234514 | A1 | 11/2004 | Sidhu |
| 2005/0232901 | A1 | 10/2005 | Zaghmout |
| 2006/0104935 | A1 | 5/2006 | Margolin et al. |
| 2007/0184118 | A1 | 8/2007 | Li et al. |
| 2008/0311101 | A1 | 12/2008 | Shenoy et al. |
| 2015/0353913 | A1 | 12/2015 | Greene et al. |
| 2016/0144094 | A1 | 5/2016 | Margolin et al. |

FOREIGN PATENT DOCUMENTS

WO    WO 2004/018634 A2    3/2004

OTHER PUBLICATIONS

Campieri et al., Kidney International, 2001, vol. 60, p. 1097-1105.*
Zelinski et al., Angew. Chem. Int. Ed. Engl., 1997, vol. 36, No. 7, p. 722-724.*
Anand et al., "Structure of Oxalate Decarboxylase from *Bacillus subtilis* at 1.75 A Resolution," Biochemistry 41:7659-7669 (2002).
Canadian Patent Application No. 2,659,081 by by Althea Technologies, Inc.: Office Action dated Dec. 9, 2013.
Chinese Patent Application No. 201310106056,0 by Althea Technologies, Inc.: First Office Action with Search Report; dated Mar. 5, 2014 (English translation, 9 pages).

(Continued)

*Primary Examiner* — Kade Ariani
(74) *Attorney, Agent, or Firm* — Goodwin Procter LLP

(57) ABSTRACT

Oxalate decarboxylase crystals, including stabilized crystals, such as cross-linked crystals of oxalate decarboxylase, are disclosed. Methods to treat a disorder associated with elevated oxalate concentration using oxalate decarboxylase crystals are also disclosed. Additionally disclosed are methods of producing protein crystals.

9 Claims, 10 Drawing Sheets

(56) References Cited

OTHER PUBLICATIONS

Dashek et al., In *Methods in Plant Biochemistry and Molecular Biology*, Boca Raton, FL: CRC Press, Chapter 5, pp. 49-71, 1997.

Earnest, "Enteric Hyperoxaluria," Adv. Internal Medicine 24:407-427 (1979).

Extended European Search Report dated Mar. 12, 2010, from European Application No. 07873799.6.

Gilliland, "A Biological Macromolecule Crystallization Database: A Basis for a Crystallization Strategy," Crystal Growth 90:51-59 (1988).

Grujic et al., "Hyperoxaluria Is Reduced and Nephrocalcinosis Prevent with an Oxalate-Degrading Enzyme in Mice with Hyperoxaluria," American Journal of Nephrology, vol. 29, No. 2, pp. 86-93 (2009).

International Preliminary Report on Patentability including the Written Opinion dated Feb. 12, 2009 from International PCT Application No. PCT/US2007/75091.

International Search Report dated Aug. 6, 2008, for PCT Application No. PCT/US2007/75091.

Leumann et al., "What is new in primary hyperoxaluria?," Nephrol. Dial. Transplant. 14:2556-2558 (1999).

Leumann et al., "The Primary Hyperoxalurias," J. Am. Soc. Nephrol. 12:1986-1993 (2001).

Magro et al., "Enzymatic oxalate decarboxylation in Isolates of Sclerotinia sclerotiorum," FEMS Microbiology Letters, 49:49-52 (1988).

Margolin, "Novel crystalline catalysts," Trends in Microbiology 14:223-30 (1996).

McPherson et al., "Crystallization of Macromolecules: General Principles," Methods Enzymol. 114:112-20 (1985).

Monico et al., "Potential mechanisms of marked hyperoxaluria not due to primary hyperoxaluria I or II," Kidney International 62:392-400 (2002).

Parkinson et al., "The determination of plasma oxalate concentrations using an enzyme/bioluminescent assay," Clin. Chim. Acta, 152(3):335-345 (1985).

Svedruzic et al., The enzymes of oxalate metabolism: unexpected structures and mechanisms, Arch. Biochem. Biophys. 433:176-192 (2005).

Tanner et al,, "Oxalate Decarboxylase Requires Manganese and Dioxygen for Activity," The Journal of Biological Chemistry 276(47):43627-43634 (2001).

Tanner et al., "*Bacillus subtilis* YvrK Is an Acid-Induced Oxalate Decarboxylase," Journal of Bacteriology 182: 5271-5273 (2000).

Vaghjiani et al., "Production and Characterisation of Cross-Linked Enzyme Crystals (CLECs®) for Application as Process Scale Biocatalysts," 18: 151-175 (2000).

Written Opinion dated Aug. 6, 2008, for PCT Application No. PCT/US2007/75091.

U.S. Appl. No. 14/761,521, Crystallized Oxalate Decarboxylase and Methods of Use, filed Jul. 16, 2015.

U.S. Appl. No. 14/896,273, Compositions, Methods, and Devices for Dialysis, filed Dec. 4, 2015.

\* cited by examiner

SEQUENCE LISTING

```
<160> NUMBER OF SEQ ID NOS: 3

<210> SEQ ID NO 1
<211> LENGTH: 1646
<212> TYPE: DNA
<213> ORGANISM: Artificial Sequence
<220> FEATURE:
<223> OTHER INFORMATION: Synthetically generated oligonucleotide

<400> SEQUENCE: 1
ataagaatgc ggccgcataa tgagatttcc atctattttt actgctgttt tatttgctgc      60
ttcttctgct ttagctgctc cagttaatac tactactgaa gatgaaactg ctcaaattcc     120
agctgaagct gttattggtt attctgattt agaaggtgat tttgatgttg ctgttttacc     180
attttctaat tctactaata atggtttatt atttattaat actactattg cttctattgc     240
tgctaaagaa gaaggtgttt ctttagaaaa aagagaagct gaagctatgt ttaataattt     300
```

```
tcaaagatta ttaactgtta ttttattatc tggttttact gctggtgttc cattagcttc    360
tactactact ggtactggta ctgctactgg tacttctact gctgctgaac catctgctac    420
tgttccattt gcttctactg atccaaatcc agttttatgg aatgaaactt ctgatccagc    480
tttagttaaa ccagaaagaa atcaattagg tgctactatt caaggtccag ataatttacc    540
aattgattta caaaatccag atttattagc tccaccaact actgatcatg gttttgttgg    600
taatgctaaa tggccatttt ctttttctaa acaaagatta caaactggtg gttgggctag    660
acaacaaaat gaagttgttt taccattagc tactaattta gcttgtacta atatgagatt    720
agaagctggt gctattagag aattacattg gcataaaaat gctgaatggg cttatgtttt    780
aaaagggtct actcaaattt ctgctgttga taatgaaggg agaaattata tttctactgt    840
tggtccaggt gatttatggt attttccacc aggtattcca cattctttac aagctactgc    900
tgatgatcca gaaggttctg aatttatttt agttttttgat tctggtgctt ttaatgatga    960
tggtactttt ttattaactg attggttatc tcatgttcca atggaagtta ttttaaaaaa   1020
ttttagagct aaaaatccag ctgcttggtc tcatattcca gctcaacaat tatatatttt   1080
tccatctgaa ccaccagctg ataatcaacc agatccagtt tctccacaag gactgttcc    1140 attaccatat tcttttaatt tttcttctgt tgaaccaact caatattctg gtgggactgc   1200
taaaattgct gattctacta cttttaatat ttctgttgct attgctgttg ctgaagttac   1260
tgttgaacca ggtgctttaa gagaattaca ttggcatcca actgaagatg aatggacttt   1320
ttttatttct ggtaatgcta gagttactat ttttgctgct caatctgttg cttctacttt   1380
tgattatcaa ggtggtgata ttgcttatgt tccagcttct atgggtcatt atgttgaaaa   1440
tattggtaat actactttaa cttatttaga agttttttaat actgatagat tgctgatgt   1500 ttctttatct caatggttag ctttaactcc accatctgtt gttcaagctc atttaaatttt  1560 agatgatgaa actttagctg aattaaaaca atttgctact aaagctactg ttgttggtcc   1620
agttaattaa gcggccgcta aactat                                        1646

<210> SEQ ID NO 2
<211> LENGTH: 1158
<212> TYPE: DNA
<213> ORGANISM: Bacillus subtilis

<400> SEQUENCE: 2
atgaaaaaac aaaatgacat tccgcagcca attagaggag acaaaggagc aacggtaaaa     60
atcccgcgca atattgaaag agaccggcaa aaccctgata tgctcgttcc gcctgaaacc    120
gatcatggca ccgtcagcaa tatgaagttt tcattctctg atactcataa ccgattagaa    180
aaaggcggat atgcccggga agtgacagta cgtgaattgc cgatttcaga aaaccttgca    240
tccgtaaata tgcggctgaa gccaggcgcg attcgcgagc ttcactggca taagaagct    300 gaatgggctt atatgattta cggaagtgca agagtcacaa ttgtagatga aaagggcgc    360 agctttattg acgatgtagg tgaaggagac ctttggtact cccgtcagg cctgccgcac    420 tccatccaag cgctggagga gggagctgag ttcctgctcg tgtttgacga tggatcattc    480
tctgaaaaca gcacgttcca gctgacagat tggctggccc acactccaaa agaagtcatt    540
gctgcgaact tcggcgtgac aaaagaagag atttccaatt gcctggcaa agaaaaatat    600 atatttgaaa accaacttcc tggcagttta aagatgata ttgtggaagg gccgaatggc    660
gaagtgcctt atccatttac ttaccgcctt cttgaacaag agccgatcga atctgaggga    720
ggaaaagtat acattgcaga ttcgacaaac ttcaaagtgt ctaaaaccat cgcatcagcg    780
```

```
ctcgtaacag tagaacccgg cgccatgaga gaactgcact ggcacccgaa tacccacgaa    840
tggcaatact acatctccgg taaagctaga atgaccgttt ttgcatctga cggccatgcc    900
agaacgttta attaccaagc cggtgatgtc ggatatgtac catttgcaat gggtcattac    960
gttgaaaaca tcggggatga accgcttgtc tttttagaaa tcttcaaaga cgaccattat   1020
gctgatgtat cttaaaacca atggcttgcc atgcttcctg aaacatttgt tcaagcgcac   1080
cttgacttgg gcaaagactt tactgatgtg ctttcaaaag aaaagcaccc agtagtgaaa   1140
aagaaatgca gtaaataa                                                 1158
```

<210> SEQ ID NO 3
<211> LENGTH: 385
<212> TYPE: PRT
<213> ORGANISM: Bacillus subtilis

<400> SEQUENCE: 3

```
Met Lys Lys Gln Asn Asp Ile Pro Gln Pro Ile Arg Gly Asp Lys Gly
  1               5                  10                  15

Ala Thr Val Lys Ile Pro Arg Asn Ile Glu Arg Asp Arg Gln Asn Pro
             20                  25                  30

Asp Met Leu Val Pro Pro Glu Thr Asp His Gly Thr Val Ser Asn Met
         35                  40                  45

Lys Phe Ser Phe Ser Asp Thr His Asn Arg Leu Glu Lys Gly Gly Tyr
     50                  55                  60

Ala Arg Glu Val Thr Val Arg Glu Leu Pro Ile Ser Glu Asn Leu Ala
 65                  70                  75                  80

Ser Val Asn Met Arg Leu Lys Pro Gly Ala Ile Arg Glu Leu His Trp
                 85                  90                  95

His Lys Glu Ala Glu Trp Ala Tyr Met Ile Tyr Gly Ser Ala Arg Val
            100                 105                 110

Thr Ile Val Asp Glu Lys Gly Arg Ser Phe Ile Asp Asp Val Gly Glu
        115                 120                 125

Gly Asp Leu Trp Tyr Phe Pro Ser Gly Leu Pro His Ser Ile Gln Ala
    130                 135                 140

Leu Glu Glu Gly Ala Glu Phe Leu Leu Val Phe Asp Asp Gly Ser Phe
145                 150                 155                 160

Ser Glu Asn Ser Thr Phe Gln Leu Thr Asp Trp Leu Ala His Thr Pro
                165                 170                 175

Lys Glu Val Ile Ala Ala Asn Phe Gly Val Thr Lys Glu Glu Ile Ser
            180                 185                 190

Asn Leu Pro Gly Lys Glu Lys Tyr Ile Phe Glu Asn Gln Leu Pro Gly
        195                 200                 205

Ser Leu Lys Asp Asp Ile Val Glu Gly Pro Asn Gly Glu Val Pro Tyr
    210                 215                 220

Pro Phe Thr Tyr Arg Leu Leu Glu Gln Glu Pro Ile Glu Ser Glu Gly
225                 230                 235                 240

Gly Lys Val Tyr Ile Ala Asp Ser Thr Asn Phe Lys Val Ser Lys Thr
                245                 250                 255

Ile Ala Ser Ala Leu Val Thr Val Glu Pro Gly Ala Met Arg Glu Leu
            260                 265                 270

His Trp His Pro Asn Thr His Glu Trp Gln Tyr Tyr Ile Ser Gly Lys
        275                 280                 285

Ala Arg Met Thr Val Phe Ala Ser Asp Gly His Ala Arg Thr Phe Asn
    290                 295                 300
```

```
Tyr Gln Ala Gly Asp Val Gly Tyr Val Pro Phe Ala Met Gly His Tyr
305                 310                 315                 320

Val Glu Asn Ile Gly Asp Glu Pro Leu Val Phe Leu Glu Ile Phe Lys
                325                 330                 335

Asp Asp His Tyr Ala Asp Val Ser Leu Asn Gln Trp Leu Ala Met Leu
            340                 345                 350

Pro Glu Thr Phe Val Gln Ala His Leu Asp Leu Gly Lys Asp Phe Thr
        355                 360                 365

Asp Val Leu Ser Lys Glu Lys His Pro Val Val Lys Lys Lys Cys Ser
    370                 375                 380

Lys
385
```

CRYSTALLIZED OXALATE DECARBOXYLASE AND METHODS OF USE

CROSS REFERENCE TO RELATED APPLICATIONS

This is a divisional of U.S. application Ser. No. 14/283,794, filed May 21, 2014 (U.S. Pat. No. 9,155,785, issued Oct. 13, 2015), which is a continuation of U.S. application Ser. No. 13/372,274, filed Feb. 13, 2012 (U.S. Pat. No. 8,741,284, issued Jun. 3, 2014), which is a divisional of U.S. application Ser. No. 11/833,082, filed Aug. 2, 2007 (U.S. Pat. No. 8,142,775, issued Mar. 27, 2012), which claims the benefit of U.S. Provisional Application No. 60/854,540, filed Oct. 26, 2006, and U.S. Provisional Application No. 60/834,933, filed on Aug. 2, 2006, all of which are incorporated herein by reference in their entireties for all purposes.

BACKGROUND

Oxalic acid is a dicarboxylic acid of the formula $HO_2C-CO_2H$. Oxalic acid exists primarily as oxalate in biological organisms, which is the salt form of oxalic acid. Oxalate is found in foods, such as, e.g., spinach, rhubarb, strawberries, cranberries, nuts, cocoa, chocolate, peanut butter, sorghum, and tea. Oxalate is also a metabolic end product in humans and other mammals. It is excreted by the kidneys into the urine. When combined with calcium, oxalic acid produces an insoluble product, calcium oxalate, which is the most prevalent chemical compound found in kidney stones.

Because mammals do not synthesize enzymes that degrade oxalate, oxalate levels in an individual are normally held in check by excretion and low absorption of dietary oxalate. Elevated concentrations of oxalate are associated with a variety of pathologies, such as primary hyperoxaluria, enteric hyperoxaluria, and idiopathic hyperoxaluria. Leumann et al., *Nephrol. Dial. Transplant.* 14:2556-2558 (1999) and Earnest, *Adv. Internal Medicine* 24:407-427 (1979). Increased oxalate can be caused by consuming too much oxalate from foods, by hyperabsorption of oxalate from the intestinal tract, and by abnormalities of oxalate production. Hypcrabsorption of oxalate in the colon and small intestine can be associated with intestinal diseases, including hyperabsorption caused by diseases of bile acid and fat malabsorption; ileal resection; and, for example, by steatorrhea due to celiac disease, exocrine pancreatic insufficiency, intestinal disease, and liver disease.

Hyperoxaluria, or increased urinary oxalate excretion, is associated with a number of health problems related to the deposit of calcium oxalate in the kidney tissue (nephrocalcinosis) or urinary tract (e.g., kidney stones, urolithiasis, and nephrolithiasis). Calcium oxalate may also be deposited in, e.g., the eyes, blood vessels, joints, bones, muscles, heart and other major organs, causing damage to the same. See, e.g., Leumann et al., *J. Am. Soc. Nephrol.* 12:1986 1993 (2001) and Monico et al., *Kidney International* 62:392 400 (2002). The effects of increased oxalate levels can appear in a variety of tissues. For example, deposits in small blood vessels cause painful skin ulcers that do not heal, deposits in bone marrow cause anemia, deposits in bone tissue cause fractures or affect growth in children, and calcium oxalate deposits in the heart cause abnormalities of heart rhythm or poor heart function.

Existing methods to treat elevated oxalate levels are not always effective and intensive dialysis and organ transplantation may be required in many patients with primary hyperoxaluria. Existing therapies for various hyperoxalurias include high-dose pyridoxine, orthophosphate, magnesium, iron, aluminum, potassium citrate, cholestyramine, and glycosaminoglycan treatment, as well as regimes for adjusting diet and fluid intake, for dialysis, and for surgical intervention, such as renal and liver transplantation. These therapies (e.g., low-oxalate or low-fat diet, pyridoxine, adequate calcium, and increased fluids), are only partially effective and they may have undesirable adverse side effects, such as the gastrointestinal effects of orthophosphate, magnesium, or cholestyramine supplementation and the risks of dialysis and surgery. Accordingly, methods that safely remove oxalate from the body are needed. Moreover, methods that degrade oxalate to reduce oxalate levels in a biological sample are advantageous over a therapy, for example, that solely blocks absorption or increased clearance of oxalate.

SUMMARY

The invention relates to crystals of oxalate decarboxylase ("OXDC") and cross-linked forms thereof ("CLEC") and their uses to treat oxalate-associated disorders, e.g., hyperoxaluria. In one embodiment, crystalline oxalate decarboxylase can be administered to a mammal, e.g., orally or directly to the stomach, to reduce oxalate levels and/or to reduce damage caused by calcium oxalate deposits in the mammal. Additionally disclosed are methods of producing protein crystals from cell extracts. Compositions, e.g., pharmaceutical compositions, including the crystals of oxalate decarboxylase ("OXDC") and cross-linked forms thereof ("CLEC") are also disclosed.

In one aspect, the invention provides cross-linked oxalate decarboxylase crystals. The cross-linking agent can be multifunctional, and in certain embodiments, the agent is a bifunctional agent, such as glutaraldehyde. In certain embodiments, the oxalate decarboxylase crystals are cross-linked with glutaraldehyde at a concentration that does not substantially alter enzyme activity, e.g., at a concentration of at least about 0.02% (w/v). In embodiments, the level of cross-linking of the oxalate decarboxylase crystal is equivalent to that produced by treatment with 0.02% (w/v) glutaraldehyde. The level of cross-linking can be determined by methods known in the art or disclosed herein, e.g., determining the level of protein leaching, e.g., as disclosed in Examples 10-11.

The invention further provides oxalate decarboxylate crystals, e.g., oxalate decarboxylate crystals that have a higher activity, e.g., at least about 100%, 200%, 300%, 400% or 500%, compared to the soluble oxalate decarboxylate.

The invention further provides a stabilized, e.g., cross-linked, oxalate decarboxylase crystal, wherein said stabilized crystal retains an activity and/or stability, in acidic conditions at least 2-, 3-fold higher than the activity and/or stability retained by a soluble oxalate decarboxylase in similar acidic conditions (e.g., an acidic pH of about 2 to 3). In embodiments, the stabilized oxalate decarboxylase crystal is at least 200%, 300%, 400% more active and/or stable than a soluble oxalate decarboxylase in acidic conditions.

The invention further provides a stabilized, e.g., cross-linked, oxalate decarboxylase crystal, wherein said stabilized crystal retains an activity and/or stability, in the presence of a protease, at least 2-, 3-fold higher than the activity and/or stability retained by a soluble oxalate decarboxylase in similar conditions. In embodiments, the stabilized oxalate decarboxylase crystal is at least 200%, 300%, 400% more active and/or stable than a soluble oxalate decarboxylase in the presence of a protease. The protease can be chosen from one or more of. e.g., pepsin, chymotrypsin or pancreatin. In embodiments, the activity of the stabilized or soluble oxalate decarboxylase is measured after exposing the stabilized crystal or soluble oxalate decarboxylase to acidic conditions and/or a protease for a predetermined length of time, e.g., at least one, two, three, four or five hours (e.g., as described in the Examples herein).

In a related aspect, the invention features a cross-linked, oxalate decarboxylase crystal which is substantially active and stable in variable pH conditions (e.g., about pH 2.5 or 3 to 7.5 or 8.5), and/or in the presence of a protease, e.g., a protease can be chosen from one or more of, e.g., pepsin, chymotrypsin or pancreatin. In embodiments, the cross-linked crystal retains an activity at least 2-, 3-fold higher than the activity retained by a soluble oxalate decarboxylase in acidic conditions (e.g., an acidic pH of about 2 to 3) and in the presence of a protease, as described herein. In other embodiments, the stabilized oxalate decarboxylase crystal is at least 200%, 300%, 400% more stable than a soluble oxalate decarboxylase in acidic conditions (e.g., an acidic pH of about 2 to 3) and in the presence of a protease, as described herein.

Compositions, e.g., pharmaceutical compositions, that include the crystals and/or the cross-linked oxalate decarboxylase crystals as described herein are also within the scope of the invention.

In some embodiments, the crystals include oxalate decarboxylase having a sequence identical or substantially identical to an oxalate decarboxylase sequence found in a natural source, such as a plant, bacterium and fungus, in particular from *Bacillus subtilis, Collybia velutipes* or *Flammulina velutipes, Aspergillus niger, Pseudomonac* sp. *Synechocystis* sp. *Streptococcus mutans, Trametes hirsute, Sclerotinia sclerotiorum, T. versicolor, Postia placenta, Myrothecium verrucaria, Agaricus bisporus, Methylobacterium extorquens, Pseudomonas oxalaticus, Ralstonia eutropha, Cupriavidus oxalaticus, Wautersia* sp., *Oxalicibacterium flavum, Ammoniiphilus oxalaticus, Vibrio oxalaticus, A. oxalativorans, Variovorax paradoxus, Xanthobacter autotrophicus, Aspergillus* sp., *Penicillium* sp., and *Mucor* species. In other embodiments, the oxalate decarboxylase is recombinantly produced.

In one aspect, the invention provides a method of reducing oxalate concentration in a subject by administering a composition, e.g., a pharmaceutical composition, that includes oxalate decarboxylase crystals, e.g., cross-linked oxalate decarboxylase crystals, as disclosed herein. In one embodiment, the oxalate decarboxylase crystals are stabilized by a cross-linking agent, such as glutaraldehyde. Administration of the composition can cause a reduction of oxalate concentration by at least 10%, at least 20%, at least 30%, or at least 40% or more. In some embodiments, the composition is administered orally or via an extracorporeal device. In one embodiment, the extracorporeal device is a catheter, e.g., a catheter coated with oxalate decarboxylase crystals. In other embodiments, the composition is administered as a suspension, dry powder, capsule, or tablet. In one embodiment, the method of reducing oxalate concentration in a mammal includes a step of assaying the oxalate concentration in a biological sample of the mammal, such as a urine, blood, plasma, or serum sample.

In another aspect, the invention provides a method of treating, preventing, and/or slowing the progression of a disorder associated with elevated oxalate concentrations in a mammal by administering oxalate decarboxylase crystals and/or stabilized, e.g., cross-linked, oxalate decarboxylase crystals to the mammal. In one embodiment, the disorder associated with elevated oxalate concentration is a kidney disorder, joint disorder, eye disorder, liver disorder, gastrointestinal disorder, or pancreatic disorder. In certain embodiments, the disorder is primary hyperoxaluria, enteric hyperoxaluria, idiopathic hyperoxaluria, ethylene glycol poisoning, cystic fibrosis, inflammatory bowel disease, urolithiasis, nephrolithiasis, chronic kidney disease, hemodialysis, and gastrointestinal bypass.

In another aspect, the invention provides a composition, e.g., a pharmaceutical composition, that includes oxalate decarboxylase crystals, e.g., cross-linked oxalate decarboxylase crystals (e.g., the crystals and/or cross-linked crystals, as disclosed herein).

In yet another aspect, the invention provides a method of treating a mammal by administering an effective amount of a pharmaceutical composition that includes oxalate decarboxylase crystals, e.g., cross-linked oxalate decarboxylase crystals (e.g., the crystals and/or cross-linked crystals, as disclosed herein).

In another aspect, the invention provides methods of producing protein crystals, e.g., enzyme crystals (e.g., oxalate decarboxylase crystals), that include: providing a preparation of cell extract or pellets/precipitate/solution containing the protein, and crystallizing the protein from the preparations. In embodiments, the methods include one or more of: culturing a prokaryotic host cell culture expressing the protein; obtaining a preparation of pellets or extracts containing desired protein; solubilizing the preparation of pellets; allowing protein crystals to form, and/or further stabilizing the crystals by cross-linking. Typically, the protein is expressed recombinantly. In embodiments, the pellet preparation includes inclusion bodies.

In embodiments, the solubilization step includes adding to the preparation of pellets one or more of: a solution comprising a mild denaturant concentration (e.g., urea or guanidine hydrochloride at a concentration, e.g., about 1 M to about 3M); a solution comprising a high salt concentration, e.g., a salt chosen from one or more of sodium chloride, potassium chloride, calcium chloride, or other salts at a concentration of, e.g., about 0.3 to about 0.8 M; a solution comprising a mild denaturant concentration under basic conditions, e.g., at a pH of about 9 to about 12; or a solution comprising a high denaturant concentration, e.g., about 4 M to about 8 M urea or guanidine hydrochloride.

In embodiments, the purifying step includes removing debris from the pellets, e.g., by separating, e.g., by one or more spinning or centrifugation steps, the solubilized preparation of pellets and/or collecting the supernatant. The purifying step may, optionally, further include passing the solubilized preparation of pellets through ion exchange chromatography, and/or filtering the solubilized preparation.

In embodiments, the crystallizing step includes concentrating the purified protein, thereby forming crystallized protein. In embodiments, the crystallized protein is obtained from the supernatant collected after the separation step, e.g., after one or more spinning or centrifugation steps. The crystallization step can additionally include contacting the crystallized protein with a cross-linking agent, e.g., a cross-linking agent disclosed herein (e.g., glutaraldehyde). The concentration of crosslinking agent used can be in the range of 0.01% to 20% w/v; typically, 0.02% to 10% w/v; more typically, 0.02%, 0.5% or 1% w/v.

In embodiments, the yield of the protein in the pellet preparation is at least about 50%, 60%, 70%, 80% of the specific protein found in the cell preparation from which the pellet preparation is obtained. In other embodiments, the yield of the solubilized protein is at least about 90%, 95% or higher of that found in the pellet preparation. In yet other embodiments, the yield of the crystallized protein is at least about 50%, 60%, 70%, 80% of that found in the pellet preparation.

The invention further provides protein crystals, e.g., enzyme crystals (e.g., oxalate decarboxylase crystals) produced by the methods disclosed herein.

The details of one or more embodiments of the invention are set forth in the accompanying drawings and the description below.

DESCRIPTION OF DRAWINGS

FIG. 5A is a section of kidney parenchyma from EG challenged mice treated with 80 mg OXDC-CLEC. FIGS. 5B and 5C are section of kidney parenchyma from the control group. The section if FIG. 5B demonstrates moderate nephrocalcinosis and the section in FIG. 5C demonstrates severe nephrocalcinosis. The dark patches are calcium oxalate deposits (example indicated by a white arrow), and the light patches are areas with interstitial fibrosis (examples indicated by gray arrows).

DETAILED DESCRIPTION

Figure 1:
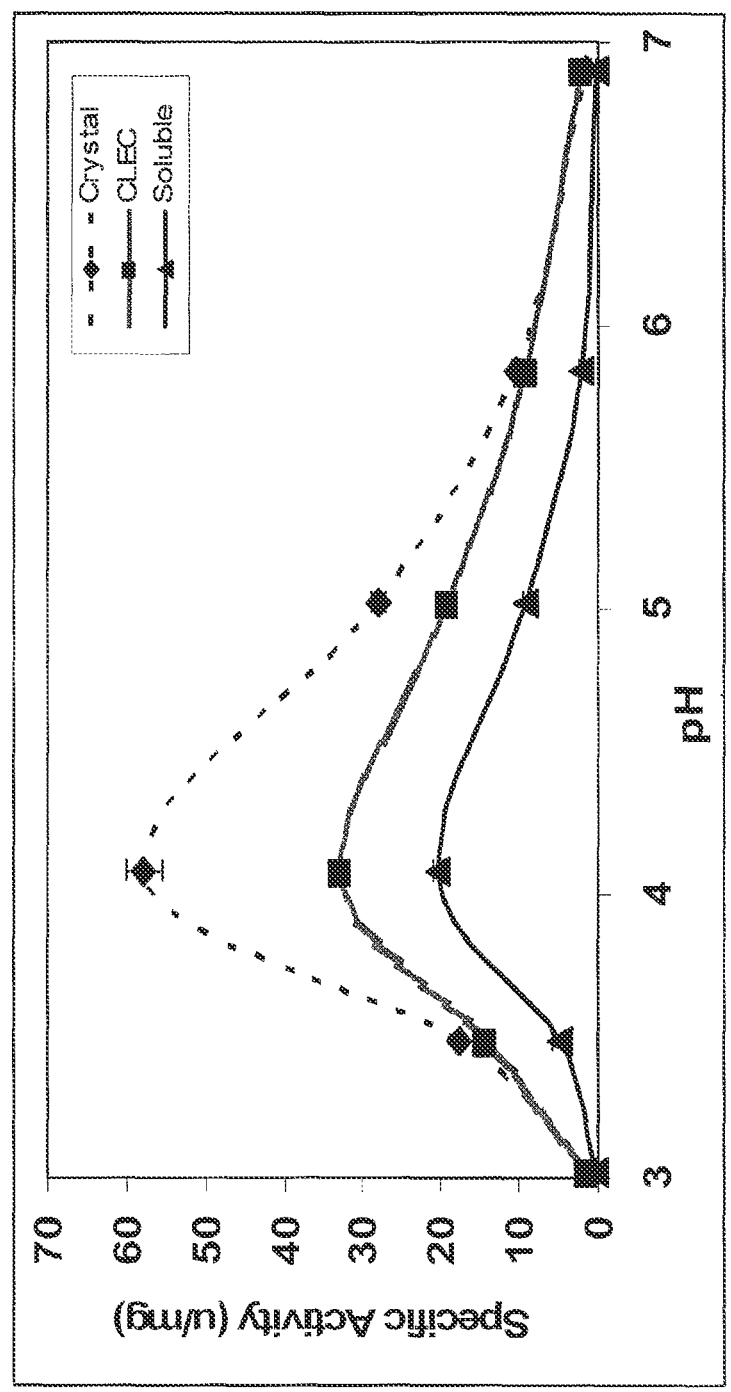
FIG. 1 is a graph showing the pH activity profile of soluble oxalate decarboxylase ("Soluble"), oxalate decarboxylase crystals ("Crystal"), and cross-linked oxalate decarboxylase crystals ("CLEC").

The present invention is based, in part, on the discovery that administering crystals of oxalate decarboxylase (OXDC) can reduce the symptoms of hyperoxaluria in a mammal. Methods of administering OXDC crystals to treat various oxalate-related disorders are described herein. Additionally, OXDC crystals and cross-linked crystals (CLECs) are provided, as are compositions comprising and using the same. Additionally disclosed are methods of producing large quantities of protein crystals from cell extracts of a prokaryotic host cell.

Definitions. In order that the present invention may be more readily understood, certain terms are first defined. Additional definitions are set forth throughout the detailed description.

As used herein, a "biological sample" is biological material collected from cells, tissues, organs, or organisms, for example, to detect an analyte. Exemplary biological samples include a fluid, cell, or tissue sample. Biological fluids include, for example, serum, blood, plasma, saliva, urine, or sweat. Cell or tissue samples include biopsy, tissue, cell suspension, or other specimens and samples, such as clinical samples.

A "crystal" is one form of the solid state of matter, comprising atoms arranged in a pattern that repeats periodically in three dimensions (see, e.g., Barret, Structure of Metals, $2^{nd}$ ed., McGraw-Hill, New York (1952)). A crystal form of a polypeptide, for example, is distinct from a second form—the amorphous solid state. Crystals display characteristic features including shape, lattice structure, percent solvent, and optical properties, such as, e.g., refractive index.

An "extracorporeal device" is a structure that is not within the body for bringing a body fluid in contact with OXDC crystals in the treatment of an individual. Preferably, an extracorporeal device is a device used for dialysis, including kidney dialysis, a device for continuous arteriovenous hemofiltration, an extracorporeal membrane oxygenator, or other device used to filter waste products from the bloodstream. Similarly, components of devices to filter waste products are encompassed by the term, including a tube, a porous material, or a membrane, for example. In particular, an extracorporeal device may be a dialysis device. It may also be a membrane of a dialysis device.

A "functional fragment" of OXDC is a portion of an OXDC polypeptide that retains one or more biological activities of OXDC, such as the ability to catalyze the decarboxylation of oxalate. As used herein, a functional fragment may comprise terminal truncations from one or both termini, unless otherwise specified. For example, a functional fragment may have 1, 2, 4, 5, 6, 8, 10, 12, 15, or 20 or more residues omitted from the amino and/or carboxyl terminus of an OXDC polypeptide. Preferably, the truncations are not more than 20 amino acids from one or both termini. A functional fragment may optionally be linked to one or more heterologous sequences.

The term "individual" or "subject" refers to any mammal, including but not limited to, any animal classified as such, including humans, non human primates, primates, baboons, chimpanzees, monkeys, rodents (e.g., mice, rats), rabbits, cats, dogs, horses, cows, sheep, goats, pigs, etc.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80% 90% (w/w) pure, even more preferably, 90 to 95% pure; and, most preferably, at least 95%, 96%, 97%, 98%, 99%, 99.5%, 99.8% or 100% (w/w) pure.

As used herein, the term "about" refers to up to ±10% of the value qualified by this term. For example, about 50 mM refers to 50 mM±5 mM; about 4% refers to 4%±0.4%.

As used herein, "oxalate-associated disorder" refers to a disease or disorder associated with pathologic levels of oxalic acid or oxalate, including, but not limited to hyperoxaluria, primarily hyperoxaluria, enteric hyperoxaluria, idiopathic hyperoxaluria, ethylene glycol (oxalate) poisoning, idiopathic urinary stone disease, renal failure (including progressive, chronic, or end-stage renal failure), steatorrhoea, malabsorption, ileal disease, vulvodynia, cardiac conductance disorders, inflammatory bowel disease, cystic fibrosis, exocrine pancreatic insufficiency, Crohn's disease, ulcerative colitis, nephrocalcinosis, urolithiasis, and nephrolithiasis. Such conditions and disorders may optionally be acute or chronic. Oxalate-associated disorders associated with kidneys, bone, liver, gastrointestinal tract, and pancreas are known in the art. Further, it is well known that calcium oxalate can deposit in a wide variety of tissues including, but not limited to, the eyes, blood vessels, joints, bones, muscles, heart, and other major organs leading to a number of oxalate-associated disorders.

"Oxalic acid" exists predominantly in its salt form, oxalate (as salts of the corresponding conjugate base), at the pH of urine and intestinal fluid ($pK_{a1}$=1.23, $pK_{a2}$=4.19). Earnest, *Adv. Internal Medicine* 24:407 427 (1979). The terms "oxalic acid" and "oxalate" are used interchangeably throughout this disclosure. Oxalate salts comprising lithium, sodium, potassium, and iron (II) are soluble, but calcium oxalate is typically very poorly soluble in water (for example, dissolving only to about 0.58 mg/100 ml at 18° C. Earnest, *Adv. Internal Medicine* 24:407 427 (1979)). Oxalic acid from food is also referred to as dietary oxalate. Oxalate that is produced by metabolic processes is referred to as endogenous oxalate. Circulating oxalate is the oxalate present in a circulating body fluid, such as blood.

The terms "therapeutically effective dose," or "therapeutically effective amount," refer to that amount of a compound that results in prevention, delay of onset of symptoms, or amelioration of symptoms of an oxalate-related condition, including hyperoxaluria, such as primary hyperoxaluria or enteric hyperoxaluria. A therapeutically effective amount will, for example, be sufficient to treat, prevent, reduce the severity, delay the onset, and/or reduce the risk of occurrence of one or more symptoms of a disorder associated with elevated oxalate concentrations. The effective amount can be determined by methods well known in the art and as described in subsequent sections of this description.

The terms "treatment," "therapeutic method," and their cognates refer to treatment of an existing disorder and/or prophylactic/preventative measures. Those in need of treatment may include individuals already having a particular medical disorder, as well as those at risk or having, or who may ultimately acquire the disorder. The need for treatment is assessed, for example, by the presence of one or more risk factors associated with the development of a disorder, the presence or progression of a disorder, or likely receptiveness to treatment of a subject having the disorder. Treatment may include slowing or reversing the progression of a disorder.

Oxalate decarboxylase. As used herein, oxalate decarboxylase (OXDC) (EC 4.1.1.2) refers to an oxalate carboxy-lyase enzyme. Oxalate decarboxylases are a group of enzymes known in the art capable of catalyzing the molecular oxygen ($O_2$) independent oxidation of oxalate to carbon dioxide and formate according to the following reaction:

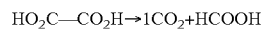

Isoforms of oxalate decarboxylase, and glycoforms of those isoforms, are included within this definition. OXDC from plants, bacteria and fungi are encompassed by the term, including the true oxalate decarboxylases from bacteria and fungi, such as *Bacillus subtilis, Collybia veltipes* or *Flammulina velutipes, Aspergillus niger, Pseudomonas* sp., *Synechocystis* sp., *Streptococcus mutans, Trametes hirsute, Sclerotinia sclerotiorum, T. versicolor, Postia placenta, Myrothecium verrucaria, Agaricus bisporus, Methylobacterium extorquens, Pseudomonas oxalaricus, Ralstonia eutropha, Cupriavidus oxalaticus, Wautersia* sp., *Oxalicibacterium flavum, Ammonliphilus oxalaticus, Vibrio oxalaticus, A. oxalativorans, Variovorox paradoxus, Xanthobacter autotrophicus, Aspergillus* sp., *Penicillium* sp., and *Mucor* species. Optionally, the OXDC will be additionally dependent on coenzyme A, such as OXDC from organisms in the intestinal tract. In certain circumstances, OXDC is a soluble hexameric protein.

Oxalate decarboxylases are produced by higher plants, bacteria, and fungi and have oxalate carboxy-lyase enzymatic activity. Oxalate decarboxylases include those produced by *Bacillus subtilis, Collybia veltipes* or *Flammulina velutipes, Aspergillus niger, Pseudomonas* sp., *Synechocystis* sp., *Streptococcus mutans, Trametes hirsute, Sclerotinia sclerotiorum, T. versicolor, Postia placenta, Myrothecium verrucaria, Agaricus bisporus, Methylobacterium extorquens, Pseudomonas oxalaricus, Ralstonia eutropha, Cupriavidus oxalaticus, Wautersia* sp., *Oxalicibacterium flavum, Ammonliphilus oxalaticus, Vibrio oxalaticus, A. oxalativorans, Variovorox paradoxus, Xanthobacter autotrophicus, Aspergillus* sp., *Penicillium* sp., and *Mucor* species are generally identified as cupin type OXDCs. The cupin-like proteins are a large class of proteins sharing certain structural features. OXDCs, such as G-OXDCs from *Collybia* sp., are active as, for example, hexameric glycoproteins.

Oxalate decarboxylases used to prepare the crystals, and which are used in methods described herein, may be isolated, for example, from a natural source, or may be derived from a natural source. As used herein, the term "derived from" means having an amino acid or nucleic acid sequence that naturally occurs in the source. For example, oxalate decarboxylase derived firm *Bacillus subtilis* will comprise a primary sequence of a *Bacillus subtilis* oxalate decarboxylase protein, or will be encoded by a nucleic acid comprising a sequence found in *Bacillus subtilis* that encodes an oxalate decarboxylase or a degenerate thereof. A protein or nucleic acid derived from a source encompasses molecules that are isolated from the source, recombinantly produced, and/or chemically synthesized or modified. The crystals provided herein may be formed from polypeptides comprising amino acid sequences of OXDC, or a functional fragment of OXDC that retains oxalate degrading activity. Preferably, the OXDC retains at least one functional characteristic of a naturally occurring OXDC, e.g., retains one or more of the ability to catalyze degradation of oxalate, ability to multimerize, and/or manganese requirement.

Isolated Oxalate Decarboxylase. Oxalate decarboxylases have been previously isolated and are thus available from many sources, including *Bacillus subtilis, Collybia veltipes* or *Flammulina velutipes*, *Aspergillus niger*, *Pseudomonas* sp., *Synechocystis* sp., *Streptococcus mutans*, *Trametes hirsute*, *Sclerotinia sclerotiorum*, *T. versicolor*, *Postia placenta*, *Myrothecium verrucaria*, *Agaricus bisporus*, *Methylobacterium extorquens*, *Pseudomonas oxalaricus*, *Ralstonia eutropha*, *Cupriavidus oxalaticus*, *Wautersia* sp., *Oxalicibacterium flavum*, *Ammonliphilus oxalaticus*, *Vibrio oxalaticus*, *A. oxalativorans*, *Variovorax paradoxus*, *Xanthobacter autotrophicus*, *Aspergillus* sp., *Penicillium* sp., and *Mucor* species. OXDC may also be purchased from commercial purveyors, such as, e.g., Sigma. Methods to isolate OXDC from a natural source are previously described, for example, in the following references: Tanner et al., *The Journal of Biological Chemistry.* 47: 43627-43634. (2001); Dashek, W. V. and Micales, J. A., *Methods in plant biochemistry and molecular biology*. Boca Raton, Fla: CRC Press. 5:49-71. (1997); Magro et al., *FEMS Microbiology Letters*. 49: 49-52. (1988); Anand et al., *Biochemistry*. 41: 7659-7669. (2002): and Tanner and Bornemann, S. *Journal of Bacteriology*. 182: 5271-5273 (2000). These isolated oxalate decarboxylases may be used to form the crystals and methods described herein.

Recombinant Oxalate Decarboxylase. Alternatively, recombinant OXDCs may be used to form the crystals and methods provided herein. In some instances, recombinant OXDCs encompass or are encoded by sequences from a naturally occurring OXDC sequence. Further, OXDCs comprising an amino acid sequence that is homologous or substantially identical to a naturally occurring sequence are herein described. Also, OXDCs encoded by a nucleic acid that is homologous or substantially identical to a naturally occurring OXDC-encoding nucleic acid are provided and may be crystallized and/or administered as described herein.

Polypeptides referred to herein as "recombinant" are polypeptides which have been produced by recombinant DNA methodology, including those that are generated by procedures which rely upon a method of artificial recombination, such as the polymerase chain reaction (PCR) and/or cloning into a vector using restriction enzymes. "Recombinant" polypeptides are also polypeptides having altered expression, such as a naturally occurring polypeptide with recombinantly modified expression in a cell, such as a host cell.

In one embodiment, OXDC is recombinantly produced from a nucleic acid that is homologous to a *Bacillus subtilis* or *Collybia* velutipes OXDC nucleic acid sequence, and sometimes it is modified, e.g., to increase or optimize recombinant production in a heterologous host. An example of such a modified sequence is provided in SEQ ID NO:1 (nucleic acid), which includes the nucleic acid sequence of the open reading frame of *Collybia velutipes* OXDC, for expression in *Candida boidinii*. The OXDC sequence has been modified to reduce its GC content, is linked to an α Mating Factor secretion signal sequence, and is flanked by engineered restriction endonuclease cleavage sites. In another embodiment, OXDC is recombinantly produced from SEQ ID NO:2, or the unmodified *Bacillus subtilis* OXDC nucleic acid sequence that is available at GenBank Accession No: Z99120. The amino acid sequence encoded by SEQ ID NO:2 is provided as SEQ ID NO:3.

OXDC polypeptides useful for forming OXDC crystals may be expressed in a host cell, such as a host cell comprising a nucleic acid construct that includes a coding sequence for an OXDC polypeptide or a functional fragment thereof. A suitable host cell for expression of OXDC may be yeast, bacteria, fungus, insect, plant, or mammalian cell, for example, or transgenic plants, transgenic animals or a cell-free system. Preferably, a host cell is capable of glycosylating the OXDC polypeptide if necessary, capable of disulfide linkages, capable of secreting the OXDC, and/or capable of supporting multimerization of OXDC polypeptides. Preferred host cells include, but are not limited to *E. coli* (including *E. coli* Origami B and *E. coli* BL21), *Pichia pastoris*, *Saccharomyces cerevisiae*, *Schizosaccharomyces pombe*, *Bacillus subtilis*, *Aspergillus*, Sf9 cells, Chinese hamster ovary (CHO), 293 cells (human embryonic kidney), and other human cells. Also transgenic plants, transgenic animals including pig, cow, goat, horse, chicken, and rabbit are suitable hosts for production of OXDC.

For recombinant production of OXDC, a host or host cell should comprise a construct in the form of a plasmid, vector, phagemid, or transcription or expression cassette that comprises at least one nucleic acid encoding an OXDC or a functional fragment thereof. A variety of constructs are available, including constructs which are maintained in single copy or multiple copy, or which become integrated into the host cell chromosome. Many recombinant expression systems, components, and reagents for recombinant expression are commercially available, for example from Invitrogen Corporation (Carlsbad, Calif.); U.S. Biological (Swampscott, Mass.); BD Biosciences Pharmingen (San Diego, Calif.); Novagen (Madison, Wis.); Stratagene (La Jolla, Calif.); and Deutsche Sammlung von Mikroorganismen und Zellkulturen GmbH (DSMZ), (Braunschweig, Germany).

Recombinant expression of OXDC is optionally controlled by a heterologous promoter, including a constitutive and/or inducible promoter. Promoters such as, e.g., T7, the alcohol oxidase (AOX) promoter, the dihydroxy-acetone synthase (DAS) promoters, the Gal 1,10 promoter, the phosphoglycerate kinase promoter, the glyceraldehyde-3-phosphate dehydrogenase promoter, alcohol dehydrogenase promoter, copper metallothionein (CUP1) promoter, acid phosphatase promoter, CMV and promoters polyhedrin are also appropriate. The particular promoter is selected based on the host or host cell. In addition, promoters that are inducible by methanol, copper sulfate, galactose, by low phosphate, by alcohol, e.g., ethanol, for example, may also be used and are well known in the art.

A nucleic acid that encodes OXDC may optionally comprise heterologous sequences. For example, a secretion sequence is included at the N-terminus of an OXDC polypeptide in some embodiments. Signal sequences such as those from α Mating Factor, BGL2, yeast acid phosphatase (PHO), xylanase, alpha amylase, from other yeast secreted proteins, and secretion signal peptides derived from other species that are capable of directing secretion from the host cell may be useful. Similarly other heterologous sequences such as linkers (e.g., comprising a cleavage or restriction endonuclease site) and one or more expression control elements, an enhancer, a terminator, a leader sequence, and one or more translation signals are within the scope of this description. These sequences may optionally be included in a construct and/or linked to the nucleic acid that encodes OXDC. Unless otherwise specified, "linked" sequences can be directly or indirectly associated with one another.

Similarly, an epitope or affinity tag such as Histidine, HA (hemagglutinin peptide), maltose binding protein, AviTag®, FLAG, or glutathione-S-transferase may be optionally linked to the OXDC polypeptide. A tag may be optionally cleavable from the OXDC after it is produced or purified. A skilled artisan can readily select appropriate heterologous sequences, for example, match host cell, construct, promoter, and/or secretion signal sequence.

OXDC homologs or variants differ from an OXDC reference sequence by one or more residues. Structurally similar amino acids can be substituted for some of the specified amino acids, for example. Structurally similar amino acids include: (I, L and V); (F and Y); (K and R); (Q and N); (D and E); and (G and A). Deletion, addition, or substitution of amino acids is also encompassed by the OXDC homologs described herein. Such homologs and variants include (i) polymorphic variants and natural or artificial mutants, (ii) modified polypeptides in which one or more residues is modified, and (iii) mutants comprising one or more modified residues.

An OXDC polypeptide or nucleic acid is "homologous" (or is a "homolog") if it is at least 40%, 50%, 60%, 70%, 75%, 80%, 85%, 90%, 95%, 97%, 98%, 99%, or 100% identical to a reference sequence. If the homolog is not identical to the reference sequence, it is a "variant." A homolog is "substantially identical" to a reference OXDC sequence if the nucleotide or amino acid sequence of the homolog differs from the reference sequence (e.g., by truncation, deletion, substitution, or addition) by no more than 1, 2, 3, 4, 5, 8, 10, 20, or 50 residues, and retains (or encodes a polypeptide that retains) the ability to catalyze the degradation of oxalate. Fragments of an oxalate decarboxylase may be homologs, including variants and/or substantially identical sequences. By way of example, homologs may be derived from various sources of OXDC, or they may be derived from or related to a reference sequence by truncation, deletion, substitution, or addition mutation. Percent identity between two nucleotide or amino acid sequences may be determined by standard alignment algorithms such as, for example, Basic Local Alignment Tool (BLAST) described in Altschul et al., *J. Mol. Biol.*, 215:403 410 (1990), the algorithm of Needleman et al., *J. Mol. Biol.*, 48:444 453 (1970), or the algorithm of Meyers et al., *Comput. Appl. Biosci.* 4:11 17 (1988). Such algorithms are incorporated into the BLASTN, BLASTP, and "BLAST 2 Sequences" programs (reviewed in McGinnis and Madden, *Nucleic Acids Res.* 32:W20-W25, 2004). When utilizing such programs, the default parameters can be used. For example, for nucleotide sequences the following settings can be used for "BLAST 2 Sequences": program BLASTN, reward for match 2, penalty for mismatch 2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON. The amino acid and nucleic acid sequences for OXDCs that are appropriate to form the crystals described herein, may include homologous, variant, or substantially identical sequences.

Purification of Oxalate Decarboxylase. Oxalate decarboxylase proteins or polypeptides may be purified from the source, such as a natural or recombinant source, prior to crystallization. A polypeptide that is referred to herein as "isolated" is a polypeptide that is substantially free of its natural environment, such as proteins, lipids, and/or nucleic acids of their source of origin (e.g., cells, tissue (i.e., plant tissue), or fluid or medium (in the case of a secreted polypeptide)). Isolated polypeptides include those obtained by methods described herein or other suitable methods, and include polypeptides that are substantially pure or essentially pure, and polypeptides produced by chemical synthesis, by recombinant production, or by combinations of biological and chemical methods. Optionally, an isolated protein has undergone further processing after its production, such as by purification steps.

Purification may comprise buffer exchange and chromatographic steps. Optionally, a concentration step may be used, e.g., by dialysis, chromatofocusing chromatography, and/or associated with buffer exchange. In certain instances, cation or anion exchange chromatography is used for purification, including Q-sepharose, DEAE sepharose, DE52, sulfopropyl Sepharose chromatography or a CM52 or similar cation exchange column. Buffer exchange optionally precedes chromatographic separation, and may be performed by tangential flow filtration such as diafiltration. In certain preparations, OXDC is at least 70%, 80%, 85%, 90%, 95%, 96%, 97%, 98%, 99%, 99.5%, 99.7%, or 99.9% pure.

Purification in gram-scale runs is appropriate to prepare OXDC, and procedures are optimized for efficient, inexpensive, manufacturing-scale OXDC purification. For example, purification of at least 0.5, 1, 2, 5, 10, 20, 50, 100, 500, or 1000 grams or more of OXDC in a purification procedure is provided. In one exemplary procedure, tangential flow filtration of starting samples of at least 10 L, 50 L, 100 L, 500 L, 1000 L or more is provided, allowing buffer exchange and precipitation of contaminant proteins. A single Q-sepharose column is optionally used for purification of OXDC.

Crystallization of purified OXDC may also remove contaminants, for example to further purify OXDC preparations. For example, OXDC crystallized as described in Examples 2-6, has reduced levels of low molecular weight contaminants, as compared to soluble purified OXDC. In some aspects, contaminants having a measured mass (by matrix assisted laser desorption ionization mass spectroscopy (MALDI-MS)) of 0-10 KDa, 1-10 KDa, 0.5-5 KDa, or 2-5 KDa are selectively excluded from the crystal form. For example, contaminants having measured masses of approximately 2.5, 3.0, 3.7, 3.8, 4.0, 4.2, or 5.0 KDa can be substantially removed by crystallization. Purification by crystallization may also be done using, e.g., crude oxalate decarboxylase containing fermentation media.

Crystallization of Oxalate Decarboxylase. Oxalate decarboxylase crystals can be prepared using an OXDC polypeptide, such as a hexamer, as described above (see Anand et al., *Biochemistry* 41:7659-7669 (2002)). Vapor diffusion (such as, e.g., hanging drop and sitting drop methods), and batch methods of crystallization, for example, can be used. Oxalate decarboxylase crystals may be grown by controlled crystallization of the protein out of an aqueous solution or an aqueous solution that includes organic solvents. Conditions to be controlled include the rate of evaporation of solvent, the presence of appropriate co-solutes and buffers, pH, and temperature, for example.

For therapeutic administration, such as to treat a condition or disorder related to oxalate levels, a variety of OXDC crystal sizes are appropriate. In certain embodiments, crystals of less than about 500 µm average dimension are administered. Oxalate decarboxylase crystals with an average, maximal, or minimal dimension (for example) that is about 0.01, 0.1, 1, 5, 10, 25, 50, 100, 200, 300, 400, 500, or 1000 µm in length are also provided. Microcrystalline showers are also suitable.

Ranges are appropriate and would be apparent to the skilled artisan. For example, the protein crystals may have a longest dimension between about 0.01 µm and about 500 µm, alternatively, between 0.1 µm and about 50 µm. In a particular embodiment, the longest dimension ranges from about 0.1 µm to about 10 µm. Crystals may also have a shape chosen from spheres, needles, rods, plates, such as hexagons and squares, rhomboids, cubes, bipyramids and prisms. In illustrative embodiments, the crystals are cubes having a longest dimension of less than 5 µm.

In general, crystals are produced by combining the protein to be crystallized with an appropriate aqueous solvent or aqueous solvent containing appropriate crystallization agents, such as salts or organic solvents. The solvent is combined with the protein and optionally subjected to agitation at a temperature determined experimentally to be appropriate for the induction of crystallization and acceptable for the maintenance of protein activity and stability. The solvent can optionally include co-solutes, such as monovalent or divalent cations, co-factors or chaotropes, as well as buffer species to control pH. The need for co-solutes and their concentrations are determined experimentally to facilitate crystallization. In an industrial scale process, the controlled precipitation leading to crystallization can be carried out by the combination of protein, precipitant, co-solutes and, optionally, buffers in a batch process, for example. Alternative laboratory crystallization methods and conditions, such as dialysis or vapor diffusion, can be adopted (McPherson, et al., *Methods Enzymol.* 114:112-20 (1985) and Gilliland, *Crystal Growth* 90:51-59 (1998)). Occasionally, incompatibility between the cross-linking agent and the crystallization medium might require changing the buffers (solvent) prior to cross-linking.

As set forth in the Examples, oxalate decarboxylase crystallizes under a number of conditions, including a wide pH range (e.g., pH 3.5 to 8.0). A precipitant such as a polyethylene glycol (such as, e.g., PEG 200, PEG 400, PEG 600, PEG 1000, PEG 2000, PEG 3000, PEG 8000 [See examples 7 and 8]) or an organic cosolvent such as 2-methyl-2,4-pentanediol (MPD) is included in some embodiments as described. Common salts that may be used include sodium chloride, potassium chloride, ammonia sulfate, zinc acetate, etc.

Oxalate decarboxylase may be at a concentration of, e.g., at least 5, 10, 15, 20, 25, 30, 35, 40, 45, 50, 60, 70, 80, 90, or 100 mg/ml, or more in a crystallization broth. The efficiency or yield of a crystallization reaction is at least 50%, 60%, 70%, 80%, 90%, 91%, 92%, 93%, 94%, 95%, 96%, 97%, 98%, 99%, or more. In one embodiment, crystals of oxalate decarboxylase are grown or produced by a batch process by mixing a solution of oxalate decarboxylase with an appropriate buffer. In certain embodiments, the buffer is 100 mM Tris-HCl buffer, pH 8.0 and 100 mM NaCl with 2 mM cysteine-HCl.

Crystallization from cells or cell extract. Crystals may be prepared directly from cells or crude cell extracts. In one embodiment, bacteria cells expressing oxalate decarboxylase are harvested. Cells are resuspended with or without DNase and homogenized. A salt solution is added to the cell lysis to reach a salt concentration of about 0.3 M, 0.4 M, 0.5 M, 0.6 M or more. The salt added can be a sodium salt, a potassium salt, a calcium salt, or other salts. Proteins may be optionally extracted from the cell mixture by removing cell debris. In one embodiment, homogenized cell mixture is centrifuged, leaving proteins in the supernatant solution. Crystals are generated by reducing salt concentration of the cell mixture or protein solution. In one embodiment, salt is removed through dialysis to maintain protein concentration. To increase crystal yield, protein solution may be concentrated before salt concentration of the solution is reduced. Crystals may be generated at a solution with a pH of about 6, 7, or 8.

Crystals may be prepared from a protein precipitate or pellet. In one embodiment, cells expressing desired proteins are harvested and oxalate decarboxylase protein is collected in a precipitate or pellet. Pellet or precipitate containing oxalate decarboxylase protein is solubilized in a salt solution. Crystals are formed by reducing salt concentration in the protein solution. For increased crystal yields, the salt concentration in the solubilized protein solution is at least about 0.3 M, 0.4 M, 0.5 M or more before it is reduced to produce crystals.

Crystals may also be prepared from a protein solution. In one embodiment, an oxalate decarboxylase protein solution is concentrated in a salt solution, and crystals are formed when the salt concentration in the solution is reduced. For increased crystal yields, the salt concentration is at least about 0.3 M, 0.4 M, 0.5 M or more before it is reduced to produce crystals.

Stabilized crystals. Once oxalate decarboxylase crystals have been grown in a suitable medium they can be optionally stabilized, such as by cross-linking. Cross-linking results in stabilization of the crystal lattice by introducing covalent links between the constituent protein molecules of the crystal. This makes possible transfer of the protein into an alternate environment that might otherwise be incompatible with the existence of the crystal lattice or even with the existence of intact protein. Oxalate decarboxylase crystals may be cross-linked through, e.g., lysine amine groups, thiol (sulfhydryl) groups, and carbohydrate moieties. Cross-linked crystals are also referred to herein as "OXDC-CLEC," "CLEC-OXDC," or "CLEC."

A cross-linked crystal may alter the enzymatic stability (e.g., pH, temperature, mechanical and/or chemical stability), the pH profile of OXDC activity, the solubility, the uniformity of crystal size or volume, the rate of release of enzyme from the crystal, and/or the pore size and shape between individual enzyme molecules in the underlying crystal lattice.

Advantageously, cross-linking or stabilizing according to the present invention is carried out in such a way that the crystals comprise an OXDC that shows at least 60%, 80%, 100%, 150%, 200%, 250%, 300% or more of the activity as compared to soluble OXDC. Stability may be increased by at least 30%, 40%, 50%, 60%, 70%, 80%, 90%, 100%, 150%, 200%, 250%, 300% or more as compared to soluble OXDC. Stability can be measured under conditions of storage, such as pH stability, temperature stability, stability against gut proteases, dissolution stability, and as in vivo biological stability, for example.

In some embodiments, cross-linking slows the dissolution of the OXDC polypeptides in the crystal into solution, effectively immobilizing the protein molecules into microcrystalline particles. Upon exposure to a trigger in the environment surrounding the cross-linked protein crystals, such as under conditions of use rather than storage, the protein molecules slowly dissolve, releasing active OXDC polypeptide and/or increasing OXDC activity. The rate of dissolution is controlled, for example, by one or more of the following factors: the degree of cross-linking, the length of time of exposure of protein crystals to the cross-linking agent, the rate of addition of cross-linking agent to the protein crystals, the nature of the cross-linker, the chain length of the cross-linker, pH, temperature, presence of sulfahydryl reagents like cysteine, glutathione, the surface area of the cross-linked protein crystals, the size of the cross-linked protein crystals, and the shape of the cross-linked protein crystals.

Cross-linking can be achieved using one or a combination of a wide variety of cross-linking agents, including a multifunctional agent, at the same time (in parallel) or in sequence. Upon exposure to a trigger in the surrounding environment, or over a given period of time, the cross-links between protein crystals cross-linked with such multifunctional cross-linking agents lessen or weaken, leading to protein dissolution or release of activity. Alternatively, the cross-links may break at the point of attachment, leading to protein dissolution or release of activity. See U.S. Pat. Nos. 5,976,529 and 6,140,475.

In some embodiments, the cross-linking agent is a multifunctional cross-linking agent having at least 2, 3, 4, 5, or more active moieties. In various embodiments, the agent may be chosen from glutaraldehyde, succinaldehyde, octanedialdehyde, glyoxal, dithiobis(succinimidylpropionate), 3,3' dithiobis(sulfosuccinimidylpropionate), dimethyl 3,3'-dithiobispropionimidate-HCl, N-succinimidyl-3-(2-pyridyldithio)propionate, hexamethylenediamine, diaminooctane, ethylenediamine, succinic anhydride, phenylglutaric anhydride, salicylaldehyde, acetimidate, formalin, acrolein, succinic semialdehyde, butyraldehyde, dodecylaldehyde, glyceraldehyde, and trans-oct-2-enal.

Additional multifunctional cross-linking agents include halo triazines, e.g., cyanuric chloride; halo-pyrimidines, e.g., 2,4,6-trichloro/bromo pyrimidine; anhydrides or halides of aliphatic or aromatic mono- or di-carboxylic acids, e.g., maleic anhydride, (meth)acryloyl chloride, chloroacetyl chloride; N-methylol compounds, e.g., N-methylol chloro-acetamide; di-isocyanates or di-isothiocyanates, e.g., phenylene-1,4-di-isocyanate and aziridines. Other cross-linking agents include epoxides, such as, for example, di-epoxides, tri-epoxides and tetra-epoxides. In one embodiment, the cross-linking agent is glutaraldehyde, a bifunctional agent, and glutaraldehyde is used alone or in sequence with an epoxide. Other cross-linking reagents (see, for example, the 1996 catalog of the Pierce Chemical Company) may also be used, at the same time (in parallel) or in sequence with reversible cross-linking agents, such as those described below.

According to an alternate embodiment of this invention, cross-linking may be carried out using reversible cross-linking agents, in parallel or in sequence. The resulting cross-linked protein crystals are characterized by a reactive multi-functional linker, into which a trigger is incorporated as a separate group. The reactive functionality is involved in linking together reactive amino acid side chains in a protein and the trigger consists of a bond that can be broken by altering one or more conditions in the surrounding environment (e.g., pH, presence of reducing agent, temperature, or thermodynamic water activity).

The cross-linking agent may be homofunctional or heterofunctional. The reactive functionality (or moiety) may, e.g., be chosen from one of the following functional groups (where R, R', R", and R'" may be alkyl, aryl or hydrogen groups):

I. Reactive acyl donors, such as, e.g.: carboxylate esters RCOOR', amides RCONHR', Acyl azides RCON$_3$, carbodiimides R—N=C=N—R', N hydroxyimide esters, RCO—O—NR', imidoesters R—C=NH$_2^+$ (OR'), anhydrides RCO—O—COR', carbonates RO—CO—O—R', urethanes RNHCONHR', acid halides RCOHal (where Hal=a halogen), acyl hydrazides RCONNR'R", and O acylisoureas RCO—O—C=NR' (—NR"R'")

II. Reactive carbonyl groups, such as, e.g.: aldehydes RCHO and ketones RCOR', acetals RCO(H$_2$)R', and ketals RR'CO2R'R" (Reactive carbonyl containing functional groups known to those well skilled in the art of protein immobilization and cross-linking are described in the literature (Pierce Catalog and Handbook, Pierce Chemical Company, Rockford, Ill. (1994); S. S. Wong, Chemistry of Protein Conjugation and Cross-linking, CRC Press, Boca Raton, Fla. (1991));

III. Alkyl or aryl donors, such as, e.g.: alkyl or aryl halides R-Hal, azides R—N$_3$, sulfate esters RSO$_3$R', phosphate esters RPO(OR'$_3$), alkyloxonium salts R$_3$O+, sulfonium esters R$_3$S+, nitrate esters RONO$_2$, Michael acceptors RCR'=CR'"COR", aryl fluorides ArF, isonitriles RN+=C—, haloamines R$_2$N-Hal, alkenes, and alkynes;

IV. Sulfur containing groups, such as, e.g.: disulfides RSSR', sulflydryls RSH, and epoxides R$_2$C_$^O$CR'$_2$; and V. Salts, such as, e.g.: alkyl or aryl ammonium salts R$_4$N+, carboxylate RCOO—, sulfate ROSO$_3$—, phosphate ROPO$_3$", and amines R$_3$N.

Reversible cross-linking agents, for example, comprise a trigger. A trigger includes an alkyl, aryl, or other chain with activating group that can react with the protein to be cross-linked. Those reactive groups can be any variety of groups such as those susceptible to nucleophilic, free radical or electrophilic displacement including halides, aldehydes, carbonates, urethanes, xanthanes, and epoxides among others. For example, reactive groups may be labile to acid, base, fluoride, enzyme, reduction, oxidation, thiol, metal, photolysis, radical, or heat.

Additional examples of reversible cross-linking agents are described in T. W. Green, Protective Groups in Organic Synthesis, John Wiley & Sons (Eds.) (1981). Any variety of strategies used for reversible protecting groups can be incorporated into a cross-linker suitable for producing cross-linked protein crystals capable of reversible, controlled solubilization. Various approaches are listed, in Waldmann's review of this subject, in *Angewante Chemie Inl. Ed. Engl.*, 35:2056 (1996).

Other types of reversible cross-linking agents are disulfide bond-containing cross-linkers. The trigger breaking cross-links formed by such cross-linking agents is the addition of reducing agent, such as cysteine, to the environment of the cross-linked protein crystals. Exemplary disulfide cross-linking agents are described in the Pierce Catalog and Handbook (1994-1995). Examples of such cross-linkers and methods are disclosed in U.S. Pat. No. 6,541,606, relevant portions of which are incorporated by reference.

In addition, cross-linking agents which cross-link between carbohydrate moieties or between a carbohydrate moiety and an amino acid may also be used.

The concentration of the cross-linking agent may be from about 0.01% to 20%, about 0.02% to 10%, or about 0.05% to 5% w/v in solution. Typically, the crosslinking agent is about 0.5% or about 1% w/v. For example, the concentration of the cross-linking agent may be, e.g., about 0.01%, 0.02%, 0.05%, 0.075%, 0.1%, 0.2%, 0.3%, 0.5%, 1%, 2%, 3%, 3.5%, 4%, 5%, 6%, 7%, 8%, 9%, 10%, 15%, or 20% w/v in solution [see Table 2 in the examples]. It may be necessary to exchange buffers prior to cross-linking. Crystals, including CLECs, may be optionally lyophilized or otherwise formulated.

The crystals, including the cross-linked crystals described herein are useful in the methods of treatment and methods to reduce oxalate levels described herein. The OXDC crystals are also useful in methods relating to industrial processes (e.g., synthesis, processing, bioremediation, disinfection, sterilization), and methods to treat plants, such as plant fungal infections, for example as reviewed in, e.g., Svedruzic et al., *Arch. Biochem. Biophys.* 433:176-192 (2005). Such non-therapeutic applications for soluble or amorphous OXDC are described, for example, in U.S. Pat. Nos. 5,866,778, 6,218,134; 6,229,065; 6,235,530; and 6,503,507. The crystals described herein can be applied to these uses, based on one or more properties of the stabilized OXDC crystals described above, such as increased stability of the oxalate decarboxylase enzyme.

Drying of Crystal of Oxalate Decarboxylase. Crystals of oxalate decarboxylase are dried by removal of water, organic solvent or liquid polymer by means including drying with $N_2$, air or inert gases, vacuum oven drying, lyophilization, washing with a volatile organic solvent followed by evaporation of the solvent, evaporation in a fume hood, tray drying, fluid bed drying, spray drying, vacuum drying, or roller drying. Typically, drying is achieved when the crystals become a free flowing powder. Drying may be carried out by passing a stream of gas over wet crystals. The gas may be selected from the group consisting of: nitrogen, argon, helium, carbon dioxide, air or combinations thereof.

In principle, dried crystals can be prepared by lyophilization. However, this technique involves rapid cooling of the material and can be applied only to freeze stable products. In one embodiment, the aqueous solution containing a crystalline oxalate decarboxylase is first frozen to between −40 and −50° C., followed by removal of the under vacuum.

Production of crystals of oxalate decarboxylase, or formulations or compositions comprising such crystals. In one aspect, crystals of oxalate decarboxylase, or formulations or compositions comprising such crystals are disclosed. Such compositions can be prepared according to the following process:

First, the oxalate decarboxylase is crystallized. Next, excipients or ingredients selected from sugars, sugar alcohols, viscosity increasing agents, wetting or solubilizing agents, buffer salts, emulsifying agents, antimicrobial agents, antioxidants, and coating agents are added directly to the mother liquor. Alternatively, the mother liquor is removed, after which the crystals are suspended in an excipient solution for a minimum of 1 hour to a maximum of 24 hours. The excipient concentration is typically between about 0.01 and about 10% (w/w). The ingredient concentration is between about 0.01 and about 90% (w/w). The crystal concentration is between about 0.01 and about 99% (w/w).

The mother liquor is then removed from the crystal slurry either by filtration or by centrifugation. Subsequently, the crystals are washed optionally with solutions of about 50 to 100% (w/w) of one or more organic solvents such as, for example, ethanol, methanol, isopropanol or ethyl acetate, either at room temperature or at temperatures between about −20° C. to about 25° C.

The crystals are then dried either by passing a stream of nitrogen, air, or inert gas over them. Alternatively, the crystals are dried by air drying, spray drying, lyophilization or vacuum drying. The drying is carried out for a minimum of about 1 hour to a maximum of about 72 hours after washing, until the moisture content of the final product is below about 10% by weight, most preferably below about 5% by weight. Finally, micromizing (reducing the size) of the crystals can be performed if necessary.

According to one embodiment of this invention, when preparing crystals of oxalate decarboxylase, or formulations or compositions comprising such crystals, enhancers, such as surfactants, are not added during crystallization. Excipients or ingredients are added to the mother liquor after crystallization, at a concentration of between about 1 and about 10% (w/w), alternatively at a concentration of between about 0.1 and about 25% (w/w), alternatively at a concentration of between about 0.1 and about 50% (w/w). The excipient or ingredient is incubated with the crystals in the mother liquor for about 0.1 to about 3 hrs, alternatively the incubation is carried out for about 0.1 to about 12 hrs, alternatively the incubation is carried out for about 0.1 to about 24 hrs.

In another embodiment of this invention, the ingredient or excipient is dissolved in a solution other than the mother liquor, and the crystals are removed from the mother liquor and suspended in the excipient or ingredient solution. The ingredient or excipient concentrations and the incubation times are the same as those described above.

Another advantage of the present invention is that crystals of oxalate decarboxylase, or formulations thereof, that are encapsulated within polymeric carriers to form compositions comprising microspheres can be dried by lyophilization. Lyophilization, or freeze-drying allows water to be separated from the composition. The oxalate decarboxylase crystal composition is first frozen and then placed in a high vacuum. In a vacuum, the crystalline water sublimes, leaving the oxalate decarboxylase crystal composition behind, containing only the tightly bound water. Such processing further stabilizes the composition and allows for easier storage and transportation at typically encountered ambient temperatures.

Spray drying allows water to be separated from the crystal preparation. It is highly suited for the continuous production of dry solids in either powder, granulate or agglomerate form from liquid feedstocks as solutions, emulsions, and pumpable suspensions. Spray drying involves the atomization of a liquid feedstock into a spray of droplets and contacting the droplets with hot air in a drying chamber. The sprays are produced by either rotary (wheel) or nozzle atomizers. Evaporation of moisture from the droplets and formation of dry particles proceed under controlled temperature and airflow conditions. Relatively high temperatures are needed for spray drying operations. However, heat damage to products is generally only slight, because of an evaporative cooling effect during the critical drying period and because the subsequent time of exposure to high temperatures of the dry material may be very short. Powder is discharged continuously from the drying chamber. Operating conditions and dryer design are selected according to the drying characteristics of the product and the powder specification. Spray drying is an ideal process where the end product must comply with precise quality standards regarding particle size distribution, residual moisture content, bulk density and particle shape.

Compositions. OXDC crystals, including cross-linked crystals are provided as a composition, such as a pharmaceutical composition (see, e.g., U.S. Pat. No. 6,541,606, describing formulations and compositions of protein crystals). Pharmaceutical compositions comprising OXDC crystals include the OXDC crystal with one or more ingredients or excipients, including, but not limited to sugars and biocompatible polymers. Examples of excipients are described in Handbook of Pharmaceutical Excipients, published jointly by the American Pharmaceutical Association and the Pharmaceutical Society of Great Britain, and further examples are set forth below.

The OXDC enzyme may be administered as a crystal in a composition as any of a variety of physiologically acceptable salt forms, and/or with an acceptable pharmaceutical carrier and/or additive as part of a pharmaceutical composition. Physiologically acceptable salt forms and standard pharmaceutical formulation techniques and excipients are well known to persons skilled in the art (see, e.g., Physician's Desk Reference (PDR) 2003, 57th ed., Medical Economics Company, 2002; and Remington: The Science and Practice of Pharmacy, eds. Gennado et al., 20th ed, Lippincott, Williams & Wilkins, 2000). For the purposes of this application, "formulations" include "crystal formulations."

Oxalate decarboxylase useful in the methods of this invention may be combined with an excipient. According to this invention, an "excipient" acts as a filler or a combination of fillers used in pharmaceutical compositions. Exemplary ingredients and excipients for use in the compositions are set forth as follows.

Biocompatible polymers. Biocompatible polymers are polymers that are non-antigenic (when not used as an adjuvant), non-carcinogenic, non-toxic and which are not otherwise inherently incompatible with living organisms may be used in the OXDC crystal compositions described herein. Examples include: poly(acrylic acid), poly(cyanoacrylates), poly(amino acids), poly(anhydrides), poly(depsipeptide), poly(esters) such as poly(lactic acid) or PLA, poly(lactic-co-glycolic acid) or PLGA, poly(β-hydroxybutyrate), poly(caprolactone) and poly(dioxanone); poly(ethylene glycol), poly((hydroxypropyl)methacrylamide, poly[(organo)phosphazene], poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

Biodegradable polymers, i.e., polymers that degrade by hydrolysis or solubilization may be included in OXDC crystal compositions. Degradation can be heterogenous (occurring primarily at the particle surface), or homogenous (degrading evenly throughout the polymer matrix).

Ingredients such as one or more excipients or pharmaceutical ingredients or excipients may be included in OXDC crystal compositions. An ingredient may be an inert or active ingredient.

Methods of Treating Oxalate-Associated Disorders with OXDC Crystals. The methods of the invention comprise administering an oxalate decarboxylase, e.g., crystals of OXDC or cross-linked forms thereof, to a mammalian subject to treat, prevent, or reduce the risk of occurrence of a condition associated with elevated levels of oxalate. The elevated levels of oxalate may be detected, e.g., in a biological sample from the subject, such as a body fluid, including urine, blood, serum, or plasma. In certain embodiments, urinary oxalate levels are detected. The crystals and/or the compositions comprising crystals may be administered in the methods described herein.

In some embodiments, methods for treating hyperoxaluria in individuals with primary hyperoxaluria, enteric hyperoxaluria, hyperoxaluria caused by surgical intervention, idiopathic hyperoxaluria, oxalosis are provided. In other instances, elevated oxalate-related disorders of the kidneys, bone, liver gastrointestinal tract and pancreas are amenable to treatment with the methods disclosed herein. Further disorders or diseases treated by the methods provided herein include, but are not limited to ethylene glycol (oxalate) poisoning, idiopathic urinary stone disease, renal failure (including progressive, chronic, or end-stage renal failure), steatorrhoea, malabsorption, ileal disease, vulvodynia, cardiac conductance disorders, inflammatory bowel disease, cystic fibrosis, exocrine pancreatic insufficiency, Crohn's disease, ulcerative colitis, nephrocalcinosis, osteoporosis, urolithiasis, and nephrolithiasis. Such conditions and disorders may optionally be acute or chronic.

The methods of the invention may reduce oxalate levels in a subject by at least 10%, 20%, 30%, 40%, 50%, 60%, 70%, 80%, 90%, 95%, or more as compared to levels in an untreated or control subject. In some embodiments, reduction is measured by comparing the oxalate level in a subject before and after administration of OXDC. In some embodiments, the invention provides a method of treating or ameliorating an oxalate-associated condition or disorder, to allow one or more symptoms of the condition or disorder to improve by at least 10%, 20%, 30%, 40%, 50%, 60%, 70%, 80%, 90%, 95% or more. In certain embodiments the methods reduce levels of endogenous oxalate and/or adsorption of dietary oxalate.

In some embodiments, methods for treating individuals having a genotype associated with high oxalate levels are provided, such as individuals homozygous or heterozygous for a mutation that reduces activity of, e.g., alanine:glyoxalate aminotransferase, glyoxylate reductase/hydroxypyruvate reductase, hepatic glycolate oxidase, or another enzyme involved in oxalate metabolism or associated with hyperoxaluria. In other embodiments, methods for treating individuals having reduced or lacking *Oxalobacter formigenes* enteric colonization are provided.

The disclosed methods include administering therapeutically effective amounts of oxalate decarboxylase to a mammalian subject at risk for, susceptible to, or afflicted with a condition associated with elevated levels of oxalate. The populations treated by the methods of the invention include, but are not limited to, subjects suffering from, or at risk for developing an oxalate-associated disorder such as, e.g., primary hyperoxaluria or enteric hyperoxaluria.

Subjects treated according to the methods of the invention include but are not limited to mammals, including humans, non human primates, primates, baboons, chimpanzees, monkeys, rodents (e.g., mice, rats), rabbits, cats, dogs, horses, cows, sheep, goats, pigs, etc.

Indications, Symptoms, and Disease Indicators. Many methods are available to assess development or progression of an oxalate-associated disorder or a condition associated with elevated oxalate levels. Such disorders include, but are not limited to, any condition, disease, or disorder as defined above. Development or progression of an oxalate-associated disorder may be assessed by measurement of urinary oxalate, plasma oxalate, measurement of kidney or liver function, or detection of calcium oxalate deposits, for example.

A condition, disease, or disorder may be identified by detecting or measuring oxalate concentrations, for example, in a urine sample or other biological sample or fluid. An early symptom of hyperoxaluria is typically kidney stones, which may be associated with severe or sudden abdominal or flank pain, blood in the urine, frequent urges to urinate, pain when urinating, or fever and chills. Kidney stones may be symptomatic or asymptomatic, and may be visualized, for example by imaging the abdomen by x-ray, ultrasound, or computerized tomography (CT) scan. If hyperoxaluria is not controlled, the kidneys are damaged and kidney function is impaired. Kidneys may even fail. Kidney failure (and poor kidney function) may be identified by a decrease in, or lacking urine output (glomerular filtration rate), general ill feeling, tiredness, and marked fatigue, nausea, vomiting, anemia, and/or failure to develop and grow normally in young children. Calcium oxalate deposits in other tissues and organs may also be detected by methods including direct visualization (e.g. in the eyes), x-ray, ultrasound, CT, echocardiogram, or biopsy (e.g., bone, liver, or kidney).

Kidney and liver function, as well as oxalate concentrations, may also be assessed using art-recognized direct and indirect assays. The chemical content or urine, blood or other biological sample may also be tested by well known techniques. For example, oxalate, glycolate, and glycerate levels may be measured. Assays for liver and kidney function are well known, such as, for example, the analysis of liver tissue for enzyme deficiencies and the analysis of kidney tissue for oxalate deposits. Samples may also be tested for DNA changes known to cause primary hyperoxaluria.

Other indications for treatment include, but are not limited to, the presence of one or more risk factors, including those discussed previously and in the following sections. A subject at risk for developing or susceptible to a condition, disease, or disorder or a subject who may be particularly receptive to treatment with oxalate decarboxylase may be identified by ascertaining the presence or absence of one or more such risk factors, diagnostic, or prognostic indicators. Similarly, an individual at risk for developing an oxalate-related disorder may be identified by analysis of one or more genetic or phenotypic markers.

The methods disclosed are useful in subjects with urinary oxalate levels of at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mg of oxalate per 24 hour period, or more. In certain embodiments, the oxalate level is associated with one or more symptoms or pathologies. Oxalate levels may be measured in a biological sample, such as a body fluid including blood, serum, plasma, or urine. Optionally, oxalate is normalized to a standard protein or substance, such as ercatinine in urine. In some embodiments, the claimed methods include administration of oxalate decarboxylase to reduce circulating oxalate levels in a subject to undetectable levels, or to less than 1%, 2%, 5%, 10%, 20%, 30%, 40%, 50%, 60%, 70%, or 80% of the subject's oxalate levels prior to treatment, within 1, 3, 5, 7, 9, 12, or 15 days.

Hyperoxaluria in humans can be characterized by urinary oxalate excretion of greater than 40 mg (approximately 440 µmol) or 30 mg per day. Exemplary clinical cutoff levels are 43 mg/day (approximately 475 µmol) for men and 32 mg/day (approximately 350 µmol) for women, for example. Hyperoxaluria can also be defined as urinary oxalate excretion greater than 30 mg per day per gram of urinary creatinine. Persons with mild hyperoxaluria may excrete at least 30-60 (342-684 µmol) or 40-60 (456-684 µmol) mg of oxalate per day. Persons with enteric hyperoxaluria may excrete at least 80 mg of urinary oxalate per day (912 µmol), and persons with primary hyperoxaluria may excrete at least 200 mg per day (2280 µmol), for example, Borowski A. E, Langman C B. *Hyperoxaluria and Oxalosis: Current Therapy and Future directions. Exp Opinion Phrama* (2006, in press).

Administration of OXDC Crystals and Compositions Thereof

Administration of oxalate decarboxylase in accordance with the methods of the invention is not limited to any particular delivery system and includes administration via the upper gastrointestinal tract, e.g., the mouth (for example in capsules, suspension, tablets, or with food), or the stomach, or upper intestine (for example by tube or injection) to reduce oxalate levels in an individual. In certain cases, the OXDC is administered to reduce endogenous oxalate levels and/or concentrations. OXDC may also be provided by an extracorporeal device, such as a dialysis apparatus, a catheter, or a structure or device that contacts a biological sample from an individual.

Administration to an individual may occur in a single dose or in repeat administrations, and in any of a variety of physiologically acceptable forms, and/or with an acceptable pharmaceutical carrier and/or additive as part of a pharmaceutical composition (described earlier). In the disclosed methods, oxalate decarboxylase may be administered alone, concurrently or consecutively over overlapping or nonoverlapping intervals with one or more additional biologically active agents, such as, e.g., pyridoxine (vitamin B-6), orthophosphate, magnesium, glycosaminoglycans, calcium, iron, aluminum, magnesium, potassium citrate, cholestyramine, organic marine hydrocolloid, plant juice, such as, e.g., banana stem juice or beet juice, or L-cysteine. Biologically active agents that reduce oxalate levels or that increase the activity or availability of OXDC are provided. In sequential administration, the oxalate decarboxylase and the additional agent or agents may be administered in any order. In some embodiments, the length of an overlapping interval may be more than 2, 4, 6, 12, 24, or 48 weeks or more.

The oxalate decarboxylase may be administered as the sole active compound or in combination with another active compound or composition. Unless otherwise indicated, the oxalate decarboxylase is administered as a dose of approximately from 10 µg/kg to 25 mg/kg or 100 mg/kg, depending on the severity of the symptoms and the progression of the disease. The appropriate therapeutically effective dose of OXDC is selected by a treating clinician and would range approximately from 10 µg/kg to 20 mg/kg, from 10 µg/kg to 10 mg/kg, from 10 µg/kg to 1 mg/kg, from 10 µg/kg to 100 µg/kg, from 100 µg/kg to 1 mg/kg, from 100 µg/kg to 10 mg/kg, from 500 µg/kg to 5 mg/kg, from 500 µg/kg to 20 mg/kg, from 1 mg/kg to 5 mg/kg, from 1 mg/kg to 25 mg/kg, from 5 mg/kg to 100 mg/kg, from 5 mg/kg to 50 mg/kg, from 5 mg/kg to 25 mg/kg, and from 10 mg/kg to 25 mg/kg. Additionally, specific dosages indicated in the Examples or in the Physician's Desk Reference (PDR) 2003, 57th ed., Medical Economics Company, 2002, may be used.

The oxalate decarboxylase crystal of the present invention may be administered through an extracorporeal device or catheter, such as for delivery of oxalate decarboxylase to a patient. Catheters, for example, urinary catheters, may be coated with compositions containing oxalate decarboxylase crystals.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

Example 1

Fermentation and Purification of Oxalate Decarboxylase

Oxalate decarboxylase (OXDC) from *Bacillus subtilis* (*B. subtilis*) is a 261 kDa homohexameric protein that consists of six identical monomers. Each monomer contains 385 amino acids, with a calculated molecular weight of ~43-44 kDa and an isoelectric point of 5.2. The OXDC gene, formerly known as yvrK, was PCR amplified using *B. subtilis* genomic DNA as template.

The amplified OXDC gene was first cloned into the pCRII vector (Invitrogen, Carlsbad, Calif.) and then subcloned and expressed from pET-11a expression vector using *E. coli* BL21 (DE3) pLysS cells. Since gene expression in the pET-11a vectors is under control of the T7 promoter. OXDC expression was regulated by induction with IPTG (isopropyl-beta-D-thiogalactopyranoside).

Fermentation was used to achieve high expression levels of recombinant OXDC in E. coli. Expression was performed in 800 L (liter) fermentation media containing casein hydrolysate (USB Corporation, Cleveland, Ohio) or soy peptone, yeast extract (USB Corporation), NaCl (Fisher Scientific), PPG 2000 anti-foam (PPG), KOH (Mallinckrodt Baker, Inc., Phillipsburg, N.J.), and ampicillin (USB Corporation). Since OXDC is a manganese-dependent enzyme, 5 mM $MnCl_2.4H_2O$ (Mallinckrodt Baker, Inc.) was included in the fermentation medium. Expression of OXDC was induced by addition of 0.4 mM IPTG (Lab Scientific). The cells expressing OXDC were grown either in shake flasks or in a fermenter. By this method, OXDC was expressed mainly in pellet preparations.

A glycerol stock of BL21 cells transformed with pET 11a-OXDC was used for fermentation. For 800 L fermentation, a pre-seed culture was prepared with 2×250 ml flasks, each containing 50 ml of medium (LB plus 100 µg/ml of ampicillin). 2×0.5 ml of inoculum was used. The cultures were incubated at 35° C., 250 rpm for 6 hours. This culture was then transferred to 6×2 L flasks each containing 1 L of media (LB plus 100 µg/ml of ampicillin). In each flask, 10 ml of starter culture was added. These cultures were incubated at 35° C., 250 rpm for 12 hours. 6 L of this culture was transferred to the 800 L fermenter containing the appropriate media as described above. The culture was grown at 37° C., pH 7.0, shaking at 100 rpm with dissolved oxygen around 30-40 until the $OD_{600}$ reached about 0.3 (this process took approximately 2-3 hours). Expression of OXDC was induced with 0.4 mM of IPTG plus 5 mM $MnCl_2.4H_2O$. The culture was induced for 4 hours at 37° C., 100 rpm. The cells were then harvested and frozen for later use. The $OD_{600}$ at the time of harvesting was about 5.5-8.0.

Cells were resuspended in a ratio of 1 kg cell paste per 4 L buffer containing 50 mM Tris pH 8, 100 mM NaCl, and in the presence or absence of 15-25 U/ml DNase. Cell suspension was blended (50-60 rpm) overnight at 4° C. The cell suspension was passed through a pre-cooled homogenizer three times on ice. The efficiency of cell lysis was checked under the microscope and unbroken cell suspension was used as a control. Cells were centrifuged at 4,000 rpm for 40 min in 1 L bottles at 4° C. Supernatant and pellet were saved for characterization by SDS-PAGE. The expression of OXDC was analyzed by SDS-PAGE. The majority of the OXDC was found in the pellet, which included inclusion bodies and other precipitates. The pellet was harvested by centrifugation at 4000 rpm for 40 min and was used immediately or frozen at −70° C. for later use.

From an 800 L fermentation reaction, we obtained between 5,000 and 5,500 g of cells, which yielded between 2,800 and 3,000 g of wet weight pellets.

Example 2

Crystallization of Oxalate Decarboxylase from Solubilized Pellets with Mild Denaturant Concentration Followed by Anion Exchange Chromatography OXDC pellets stored frozen at −20° C. were used to prepare crystals of OXDC.

In this procedure, pellets were solubilized under mild conditions of denaturant concentration and pH. The solubilized protein was then refolded using an anion exchange matrix column.

The pellets were solubilized in 2 M Urea, 100 mM Tris pH 10.0, 10 mM DTT and 100 mM NaCl (1:10 w/v). The solution was stirred at room temperature (RT) for 2 h, and then the solution was centrifuged at 15 K for 30 min at 4° C. The supernatant was carefully decanted and saved. The pellet was carefully weighed and saved separately.

The solubilized pellets in supernatant were added dropwise, at a flow rate of 10 ml/min, to 10 vol. of a solution consisting of 2 M Urea, 100 mM Tris pH 8.0, 1 mM DTT, and 1 mM $MnCl_2$, with constant and gentle stirring. After complete addition of the supernatant the protein solution was incubated at RT for 1 h. After incubation, the protein solution was made ready for anion exchange chromatography by centrifuging at 15 K for 30 min at 4° C. to remove any possible precipitation.

An anion exchange chromatography column was prepared by packing Q sepharose matrix in glass column. The column was attached to an FPLC and equilibrated by washing with 10 column volumes (CV) of a solution of 0.5 M Urea, 100 mM Tris pH 8.0, 1 mM DTT, and 1 mM $MnCl_2$. The flow-rate was maintained at 6 ml/min. Solubilized pellet was loaded onto the column. Protein load was 8-10 mg/ml of matrix. After loading the sample, the column was washed with at least 10 CV of 100 mM Tris pH 8.0, 1 mM DTT and 1 mM $MnCl_2$ at a flow rate of 6 ml/min. This step removed urea from the bound protein sample and allowed the protein to refold to its native conformation.

The protein was eluted from the column with 1M NaCl, 100 mM Tris pH 8.0, and 1 mM DTT by either a step gradient or by step elution. The protein elution was monitored at 280 nm and fractions of 10 ml were collected. The peak fractions were pooled together and tested by SDS-PAGE and enzyme activity.

The peak fractions containing OXDC were concentrated to 15 mg/mL by stirring cells using a 10,000 MWCO membrane, and dialyzing against 10 vol. of 100 mM Tris pH 8.0, 100 mM NaCl, and 1 mM DTT. Two changes of buffer were made at one hour intervals and after a third change of buffer, the dialysis continued overnight for maximum crystal recovery. Protein crystallized in dialysis bags was recovered by centrifuging the sample at 2K, for 15 min at 4° C. After dialysis, about 70% of the refolded OXDC was crystallized. The crystals were cubic in shape and of uniform size. The crystals showed an activity of ~44 units.

Example 3

Crystallization of Oxalate Decarboxylase by Solubilizing Pellets Using High Denaturant Concentration Followed by Anion Exchange Chromatography By this method, pellets were solubilized in 5 M urea, 50 mM Tris pH 8.6, 100 mM NaCl, 10 mM DTT (1:5 w/v). The solution was stirred at RT for 2 h, and then the solution was centrifuged at 15K for 30 min at 4° C. The supernatant was carefully decanted and saved. The pellet was weighed and saved separately.

Anion exchange chromatography column was prepared by packing Q sepharose matrix in glass column. The column was attached to an FPLC and equilibrated by washing with 3 column volumes (CV) of the 4 M Urea, 100 mM Tris pH 8.6 and 10 mM DTT. The column was further washed with 7 CV in 100 mM NaCl, 50 mM Tris pH 8, 1 mM $MnCl_2$, 10 mM DTT and eluted in a single step with 3 CV of 0.5 M NaCl, 50 mM Tris pH 8.0, 1 mM DTT, 1 mM $MnCl_2$.

Appropriate fractions were collected and the protein was identified by SDS-PAGE and activity assay. The soluble protein was concentrated in the presence of high salt (0.5 M NaCl). A total volume of 450 ml was eluted with 0.5 M salt and concentrated to 45 ml with pellicon filtration into 100 mM NaCl, 50 mM Tris pH 8.0, 1 mM DTT. After protein concentration, dilution was performed in order to reduce the salt concentration from 0.5 M to 0.1 M NaCl. At this point, crystals of OXDC began to form. In this example, the volume was brought to 210 mL in 100 mM NaCl, 50 mM Tris pH 8.0, 1 mM DTT equivalent. Formed crystals were spun and recovered in 100 mM NaCl, and 50 mM Tris pH 8.0, in the presence or absence of 1 mM DTT.

Example 4

Crystallization of Oxalate Decarboxylase by Solubilizing Pellets Using High pH and Mild Denaturant Concentration Followed by Concentration on Hollow Fiber Pellets containing inclusion bodies and other precipitates (3.93 kg) were solubilized in 9.5 L of 50 mM Tris pH 12, 500 mM NaCl, 2 M urea, 10 mM DTT for 2 hours at room temperature. Final volume was 12 L, pH 9.9. The sample was spun at 7000 rpm for 45 minutes and supernatant was recovered. The total volume after spinning was 11.1 L, pH 9.9. The sample was concentrated on hollow fiber to 5 L for an hour and the volume was then slowly brought up to 20 L with 50 mM Tris pH 8.0, 500 mM NaCl, 2 M urea, 10 mM DTT. This process was done for an hour. The final concentration of urea at this point is estimated around 0.5 M urea. The volume was concentrated to 6 L in hollow fiber for 2.5 h. The sample was diluted to 24 L with 50 mM Tris pH 8.0, 500 mM NaCl, 1 mM DTT, 1 mM $MnCl_2$, 200 mM L-Arginine for 30 min. At this point the concentration of urea was estimated to be 125 mM. Another round of concentration was done to a final volume of 5 L. The sample was diluted to 18 L with 50 mM Tris pH 8.0, 500 mM NaCl, 1 mM DTT, 1 mM $MnCl_2$ and concentrated again to 6.5 L. The pH was at this time 8.1. The sample was spun 45 minutes at 7000 rpm and the final pellet was saved for analysis. After centrifugation, a dilution step with 50 mM Tris pTH 8.0, 1 mM DTT, was performed to obtain crystals. The dilution was to 30 L using a peristaltic pump, with mixing, at room temperature. The flow rate of dilution was estimated to be 50 ml/min. This dilution took about 9 hours. Crystals were harvested by centrifugation and the supernatant was saved for analysis. The crystals were washed three times with 50 mM Tris, 100 mM NaCl pH 8 and resuspended in 50 mM Tris, 100 mM NaCl pH 8. The crystals were stored at 4° C.

Example 5

Crystallization of Oxalate Decarboxylase from Cell Extracts Using High Salt (1) Crystallization by Solubilizing Protein-Containing Pellets Using High Salt Concentration Followed by Concentration and Dilution Frozen pellets (465 g) of Example 1 were solubilized in 2.3 L 100 mM Tris, 1 mM L-cystein HCL, 0.5 M NaCl, pH 8.0, for 2 hours at room temperature, forming soluble oxalate decarboxylase. The sample was spun at 7000 rpm for 45 minutes and supernatant was recovered. The final volume was 2.15 L and the protein concentration measured was 24.14 mg/ml. The sample was concentrated to 550 ml by tangential flow filtration (10 kD Pall) for an hour, and then diluted to 2,750 L with 100 mM Tris pH 8.0, 1 mM L-cysteine HCl over 30 minutes at a flow rate of 73 ml/min and stirring for an hour at room temperature. Crystals were allowed to form overnight in the cold room. Crystals were harvested by centrifugation, and the supernatant was saved for analysis. The crystals were washed three times with 100 mM Tris, 100 mM NaCl pH 8 and then resuspended in 100 mM Tris, 100 mM NaCl pH 8. The crystals were stored at 4° C. Recombinant *B. subtilis* OXDC purified from *E. coli* expression medium exhibits a specific activity of about 50-60 U/mg under standard assay conditions (see Example 15).

(2) Crystallization by Solubilizing Pellets Using High Salt Concentration Followed by Concentration and Dialysis Frozen pellets (510 g) of Example 1 were solubilized in 3 L 100 mM Tris, 1 mM L-cysteine HCL, 0.5 M NaCl, pH 8.0, for 2 hours at room temperature. The sample was spun at 7000 rpm for 30 minutes and supernatant was recovered. The sample was concentrated to 500 ml by tangential flow filtration (10 kD Pall) for an hour, and then dialyzed against 100 mM Tris pH 8.0 with stirring. Crystals were allowed to form overnight in the cold room. Crystals were harvested by centrifugation, and the supernatant was saved for analysis. The crystals were washed three times with 100 mM Tris, pH 8.0 and then resuspended in 100 mM Tris pH 8.0. The crystals were stored at 4° C. The crystal yield was 60%.

(3) Crystallization by Solubilizing Pellets Using High Salt Concentration Followed by Concentration and Dialysis Frozen pellets (510 g) of Example 1 were solubilized in 3 L 100 mM Tris, 1 mM L-cysteine HCL, 0.5 M NaCl, pH 8.0, for 2 hours at room temperature. The sample was spun at 7000 rpm for 30 minutes and supernatant was recovered. The sample was concentrated to 500 ml by tangential flow filtration (10 kD Pall) for an hour, and then dialyzed against 100 mM Tris pH 7.5 with stirring. Crystals were allowed to form overnight in the cold room. Crystals were harvested by centrifugation, and the supernatant was saved for analysis. The crystals were washed three times with 100 mM Tris, pH 7.5 and then resuspended in 100 mM Tris pH 7.5. The crystals were stored at 4° C. The crystal yield was 67%.

(4) Crystallization by Solubilizing Pellets Using High Salt Concentration Followed by Concentration and Dialysis Frozen pellets (510 g) of Example 1 were solubilized in 3 L 100 mM Tris, 1 mM L-cysteine HCL, 0.5 M NaCl, pH 8.0, for 2 hours at room temperature. The sample was spun at 7000 rpm for 30 minutes and supernatant was recovered. The sample was concentrated to 500 ml by tangential flow filtration (10 kD Pall) for an hour, and then dialyzed against 100 mM Tris pH 7.0 with stirring. Crystals were allowed to form overnight in the cold room. Crystals were harvested by centrifugation, and the supernatant was saved for analysis. The crystals were washed three times with 100 mM Tris, pH 7.0 and then resuspended in 100 mM Tris pH 7.0. The crystals were stored at 4° C. The crystal yield was about 80%.

(5) Crystallization by Solubilizing Pellets Using High Salt Concentration Followed by Concentration and Dialysis Frozen pellets (510 g) of Example 1 were solubilized in 3 L 100 mM Tris, 1 mM L-cysteine HCL, 0.5 M NaCl, pH 8.0, for 2 hours at room temperature. The sample was spun at 7000 rpm for 30 minutes and supernatant was recovered. The sample was concentrated to 500 ml by tangential flow filtration (10 kD Pall) for an hour, and then dialyzed against 100 mM sodium citrate buffer pH 6.5 with stirring. Crystals were allowed to form overnight in the cold room. Crystals were harvested by centrifugation, and the supernatant was saved for analysis. The crystals were washed three times with 100 mM sodium citrate buffer, pH 6.5 and then resuspended in 100 mM sodium citrate buffer pH 6.5. The crystals were stored at 4° C. The crystal yield was about 70%.

(6) Crystallization by Solubilizing Pellets Using High Salt Concentration Followed by Concentration and Dialysis Frozen pellets (510 g) of Example 1 were solubilized in 3 L 100 mM Tris, 1 mM L-cysteine HCL, 0.5 M NaCl, pH 8.0, for 2 hours at room temperature. The sample was spun at 7000 rpm for 30 minutes and supernatant was recovered. The sample was concentrated to 500 ml by tangential flow filtration (10 kD Pall) for an hour, and then dialyzed against 100 mM sodium citrate buffer pH 6.0 with stirring. Crystals were allowed to form overnight in the cold room. Crystals were harvested by centrifugation, and the supernatant was saved for analysis. The crystals were washed three times with 100 mM sodium citrate buffer, pH 6.0 and then resuspended in 100 mM sodium citrate buffer pH 6.0. The crystals were stored at 4° C. The crystal yield was about 60%.

(7) Crystallization of OXDC from Cell Paste after Homogenization and Solubilization Cells were resuspended in a ratio of 1 kg cell paste per 3 L buffer containing 100 mM Tris pH 7.5, 500 mM NaCl, 5 mM cysteine, and 1 mM manganese chloride. Cell suspension was blended (50-60 rpm) overnight at 4° C. The cell suspension was passed through a pre-cooled homogenizer two times on ice. The efficiency of cell lysis was checked under the microscope and unbroken cell suspension was used as a control. The suspension was made up to 10 L and mixed with overhead stirrer for 3 hrs at room temperature. The crude extract was then centrifuged at 7,000 rpm for 30 min at 4° C. and supernatant was recovered. Supernatant and pellet were saved for characterization by SDS-PAGE. The expression of OXDC was analyzed by SDS-PAGE. The majority of the OXDC was found in the supernatant. The final volume was 10 L and the protein concentration measured was 34 mg/ml. The sample was concentrated to 3.5 L by tangential flow filtration (10 kD Pall) for an hour, and then diluted using crystallization buffer (100 mM Tris, 100 mM NaCl pH 7.5) with stirring for an hour at room temperature. Crystals were harvested by centrifugation, and the supernatant was saved for analysis. The crystals were washed three times with 100 mM Tris, 100 mM NaCl pH 7.5 and then resuspended in 100 mM Tris and 100 mM NaCl, pH 7.5. The crystals were stored at 4° C.

Example 6

Crystallization of OXDC from Soluble Protein

OXDC was expressed in E. coli in a shaking flask. The cells were lysed by microfluidizer with 25 mM Tris-HCl buffer, pH 8.0, 100 mM NaCl containing 25 U/ml of DNase 1. The cell lysate was incubated at room temperature for one hour to allow OXDC crystals to form. The crystals were spun down and reconstituted in 100 mM Tris, 100 mM NaCl pH 8.

Example 7

Crystallization of OXDC by Vapor Diffusion

Hanging drop crystallization trials were performed using commercially available sparse matrix crystallization kits: Crystal Screen (Hampton Research; Aliso Viejo, Calif.), Crystal Screen 2 (Hampton Research), Wizard I (Emerald Biosystems; Bainbridge Island, Wash.), Wizard II (Emerald Biosystems). Cryo I (Emerald Biosystems), and Cryo II (Emerald Biosystems).

600 µl of reagent was placed in each well. 3 µl of reagent was dispensed onto a glass microscope coverslip and 3 µl of OXDC was dispensed into the reagent drop with minimal mixing. Up to five more drops were made from this 6 µl reagent and OXDC drop. As the drops were minimally mixed, each of the subsequent (smaller) drops had a different and unknown ratio of protein to reagent, thereby increasing the likelihood of obtaining crystals in a short period of time. The hanging drops were examined for crystals under a microscope after overnight incubation at room temperature. A large number of crystallization conditions were obtained, as shown in Table 1.

TABLE 1

Crystallization conditions for OXDC in hanging drops.[a]

| Precipitant | Description of Crystals |
| --- | --- |
| 40% (v/v) Ethanol, 0.1M phosphate citrate, pH 4.20, 5% (w/v) PEG 1000 | needles |
| 20% (w/v) PEG-3000, 0.1M HEPES, pH 7.50, 0.2M NaCl | rods |
| 20% (w/v) PEG-3000, 0.1M acetate pH 4.5 | Rods, plates |
| 20% (w/v) PEG 8000, 0.1M phosphate-citrate, pH 4.20, 0.2M NaCl | plates |
| 10% (w/v) PEG 8000, 0.1M Cacodylate, pH 6.50, 0.2M Magnesium acetate | rods |
| 9% (w/v) PEG 8000, 0.1M Cacodylate, pH 6.50, 0.2M Calcium acetate | needles |
| 40% (v/v) PEG 400, 0.1M Na/phosphate, pH 6.20, 0.2M NaCl | needles |
| 10% (v/v) PEG 8000, 0.1M Na/phosphate, pH 6.20, 0.2M NaCl | rods |
| 20% (w/v) PEG 2000 MME, 0.1M Tris, pH 7.0 | plates |

[a]OXDC concentration was determined by Bradford assay to be about 1.7 mg/mL.

Example 8

Crystallization of OXDC by Microbatch

Oxalate decarboxylase could be crystallized by the microbatch method from a number of crystallization conditions:

(i) 10 µl of purified OXDC at a concentration of 23.46 mg/ml was mixed with 10 µl of 16% PEG 8000. Crystallization occurred immediately in 2-5 seconds. Big crystals formed with some precipitates.

(ii) 10 µl of purified OXDC at a concentration of 23.46 mg/ml was mixed with 10 µl of 20% PEG 8000. Crystallization occurred immediately in 2-5 seconds. Big crystals formed with no precipitates.

(iii) 10 µl of purified OXDC at a concentration of 23.46 mg/ml was mixed with 10 µl of 24% PEG 8000. Crystallization occurred immediately in 2-5 seconds. Smaller cube shaped crystals formed.

(iv) 10 µl of purified OXDC at a concentration of 23.46 mg/ml was mixed with 10 µl of 28% PEG 8000. Crystallization occurred immediately in 2-5 seconds. Very small cube shaped crystals formed. There was no precipitation.

(v) 8 µl of purified OXDC at a concentration of 23.46 mg/ml was mixed with 12 µl of 24% PEG 8000. Crystallization occurred immediately in 2-5 seconds. Very small cube shaped crystals formed. There was no precipitation.

(vi) 9 µl of purified OXDC at a concentration of 23.46 mg/ml was mixed with 11 µl of 24% PEG 8000. Crystallization occurred immediately in 2-5 seconds. Small cube shaped crystals formed. There was no precipitation.

(vii) 10 µl of purified oxalate decarboxylase at a concentration of 23.46 mg/ml was mixed with 10 µl of 24% PEG 8000. Crystallization occurred immediately in 2-5 seconds. Small cube shaped crystals formed. There was no precipitation.

(viii) 11 µl of purified oxalate decarboxylase at a concentration of 23.46 mg/ml was mixed with 9 µl of 24% PEG 8000. Crystallization occurred immediately in 2-5 seconds. Cube shaped crystals formed. There was no precipitation.

(ix) 12 µl of purified OXDC at a concentration of 23.46 mg/ml was mixed with 8 µl of 24% PEG 8000. Crystallization occurred immediately in 2-5 seconds. Cube shaped crystals formed. There was no precipitation.

Example 9

Activities of Soluble OXDC and OXDC Crystals

Soluble OXDC was collected as described in Example 5 after the pellets were solubilized, spun and the supernatant recovered. OXDC crystals were collected as described in Example 5 after the crystals were harvested and washed. Activities of soluble OXDC and OXDC crystals were measured according to Example 15. In one experiment, the activity of soluble OXDC was 12 Units/mg, and the activity of OXDC crystal was 35 Units/mg.

Soluble OXDC is collected as described in any of Examples 2-5 and OXDC crystals are harvested as described in any of Examples 2-8. Activities of soluble and crystal OXDC are measured according to Example 15. Activities of OXDC crystals can be at least about 100%, 200%, 300%, 400% or 500% of the activities of soluble OXDC.

Example 10

Cross-linking of Oxalate Decarboxylase Crystals with Glutaraldehyde

Oxalate decarboxylase crystals prepared according to any of the Examples 2-8 were cross-linked using glutaraldehyde. After crystallization, OXDC crystals were concentrated to 20-30 mg/ml. 0.8 ml of 25% glutaraldehyde was added to 20 ml of crystals to make a solution of 1% glutaraldehyde, and crystals were tumbled for 18 hours at room temperature. Cross-linked crystals were washed five times with 100 mM Tris, pH 7.00 and resuspended in 10 mM Tris, pH 7.00.

Specific activities of crystalline OXDC and cross-linked OXDC (referred to as OXDC-CLEC) were compared (six trials) and it was shown that cross-linked oxalate decarboxylase crystals retain more than 30% to more than 50% of the original activity of the crystalline protein, in various preparations.

To test the effects of varying concentrations of glutaraldehyde on enzyme activity, 1 ml aliquots of OXDC crystals (60 mg/ml) were crosslinked with different concentrations of glutaraldehyde (from 0.05% to 2%, final concentration) at pH 8.0 at 25° C. for 18 hrs. The crosslinking was terminated by separation of the crosslinked crystals by centrifugation at 2000 rpm in an eppendorf tube and then resuspension of the crosslinked crystals in 1 ml of 100 mM Tris-HCl, pH 7.0. The cross-linked OXDC (OXDC-CLEC) was then washed five times with 100 mM Tris-HCl buffer, pH 7.5, followed by three washes with 10 mM Tris-HCl buffer, pH 7.5 (see results in Table 2, below).

Example 11 pH Controlled Solubility of Crosslinked Oxalate Decarboxylase Crystals

Solubility of various crosslinked oxalate decarboxylase crystals was examined following a decrease in pH from 7.5 to 3.0. The cross-linked crystals were incubated at 1 mg/ml in 50 mM glycine.HCl (pH 3.0). Aliquots were removed after 5 hour incubation at 37° C. with stirring. Soluble protein concentration was measured at $OD_{280}$ nm after separation of the undissolved crosslinked crystals by centrifugation at 2000 rpm and filtration of the supernatant through 0.22 µm filter. The results are described in Table 2 below.

TABLE 2

Crosslinking of OXDC Crystals with Different Percentages of Glytaraldehyde and pH-Controlled Solubility of OXDC-CLEC

| Sample | % Glutaraldehyde | % Protein Leaching |
|---|---|---|
| OxDc-CLEC-1 | 0.005 | 100.0 |
| OxDc-CLEC-2 | 0.010 | 100.0 |
| OxDc-CLEC-3 | 0.050 | 2.2 |
| OxDc-CLEC-4 | 0.075 | 0.0 |
| OxDc-CLEC-5 | 0.100 | 0.0 |
| OxDc-CLEC-6 | 0.200 | 0.0 |
| OxDc-CLEC-7 | 1.000 | 0.0 |

These results indicate that a substantially stable glutaraldehyde OXDC crosslinked crystal is formed in the presence of at least about 0.05% (final concentration) glutaraldehyde.

Example 12 pH Activity Profile of Soluble OXDC, Crystalline OXDC, and OXDC-CLEC

Oxalate decarboxylase crystals, prepared as described in Examples 2-8, were crosslinked by addition of glutaraldehyde (Sigma). A 1 ml aliquot of OXDC crystals (30-40 mg/ml) was crosslinked with 1% glutaraldehyde (final concentration) at pH 8.0 at 25° C. or 18 hrs. The crosslinking was terminated by separation of the crosslinked crystals by centrifugation at 2000 rpm in an eppendorf tube and then resuspension of the crosslinked crystals in 1 ml of 100 mM Tris HCl, pH 7.0. The OXDC-CLEC was then washed five times with 100 mM Tris-HCl buffet; pH 7.0, followed by three washes with 10 mM Tris-HCl buffer, pH 7.0. The pH activity profile of OXDC-CLEC was assayed by measuring the activity of the crystals as described in Example 15 using various buffers and pHs: 50 mM glycine.HCl buffer at pH 2.0 and 3.0; 50 mM succinate buffer at pHs 4.0, 5.0, and 6.0; and 50 mM Tris buffer at pH 7.0. The activity level at each pH was performed twice and the average activity was calculated. The results, shown in FIG. 1, indicate that OXDC-CLEC is most active than its soluble counterpart between pH 3.5 and 6.0. The uncrosslinked crystals showed much higher activity, ranging from about 50% to about 200%, 300% or 400% more, than the soluble form of oxalate decarboxylase at different pH.

Example 13

Oxalate Decarboxylase Therapy in Animal Model for Enteric Hyperoxaluria

Rat Model for Enteric Hyperoxaluria, Dose Range Study: Male Sprague Dawley (SD) rats fed a diet high in oxalate constitute a suitable animal system for the study of enteric hyperoxaluria. In this study, administration of 1.1% dietary potassium oxalate resulted in a 5- to 10-fold increase in urinary oxalate.

Twenty Sprague Dawley (SD) rats less than 35 days old and weighing 100-120 grams were randomly divided into a control group and experimental groups (five rats per group). Rats were acclimated for 7 days to individual metabolic cages (LabProducts, Inc.; Seaford, Del.) prior to treatment. During this period, rats were provided ad libitum with supplemented acidified water and fed a synthetic diet having 1.1% potassium oxalate and a low (0.5%) concentration of calcium (Research Diets TD89222PWD; Harlan Teklad; Madison, Wis.). Rats were maintained on this diet for the duration of the treatment.

Following the acclimation period, three different doses of recombinant oxalate decarboxylase, formulated as cross-linked crystals with 1% glutaraldehyde (see, e.g., Example 9), were administered to the test rats for 4 consecutive weeks. The crystals were administered orally as a freeze/dried food enzyme mixture (5, 25 and 80 mg of OXDC-CLEC slurry in 10 mM Tris-HCl pH 7.0, each separately mixed with 15 g food and freeze dried; each morning, food containers were re-filled with ~20 g of food/enzyme mixture). Prior to the treatment, rats were randomly divided between a control group and experimental group based on their basal urinary oxalate.

Analysis of urine samples: 24 hour urinary samples were collected in metabolic cages over acid (250 µl of 6N hydrochloride acid was mixed with urine sample collected during 24 h) in order to minimize the spontaneous breakdown of urinary ascorbic acid to oxalate. Samples were stored at −70° C. until further analysis. Daily diuresis and multiple 24 h (hour) urine samples were collected for oxalate and creatinine measurements. Assays for oxalate and creatinine are described in Example 15. Urinary excretion of oxalate and creatinine were expressed as µmol of oxalate and creatinine detected in 24 h urine samples. All data were analyzed statistically using the Student's t-test.

Figure 2:
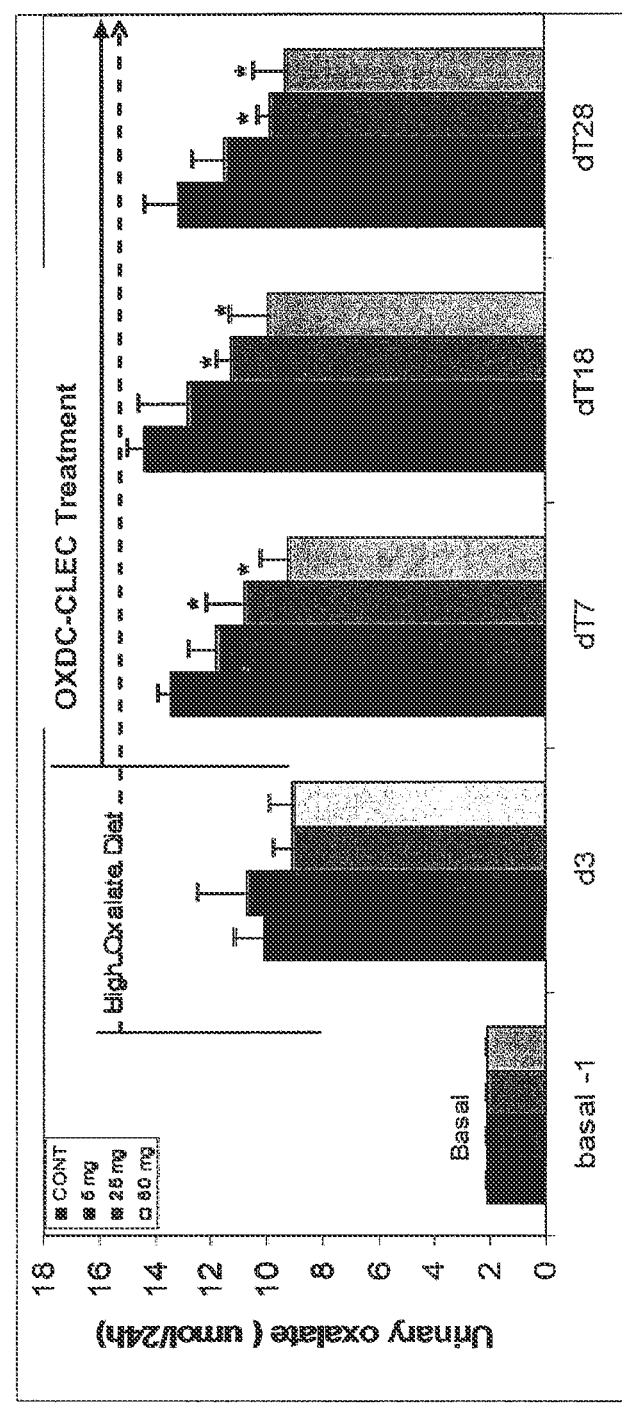
FIG. 2 is a bar graph depicting urinary oxalate levels in Sprague Dawley rats after administration of OXDC-CLEC. Each bar represents a mean±SE (standard error). The asterisks indicate a significant difference between the control group and three treatment groups at p<0.05 at the time point, using a two tailed Student t-test.

As shown in FIG. 2, oral administration of OXDC-CLEC to SD rats with chronic hyperoxaluria resulted in a sustained reduction of urinary oxalate from day 4 of the treatment. Maximal continuous reduction between 25-40% was recorded in the highest dose group (80 mg OXDC-CLEC). The lower doses of 5 mg and 25 mg OXDC-CLEC produced smaller reduction in urinary oxalate (up to 30% in the 25 mg group and 20% in the 5 mg group, respectively). The doses of 25 mg and 80 mg produced significant reduction during all tested days (except day 21 for 25 mg group), while the lowest dose of 5 mg had a minimal effect which was not significant. This result reveals a dose dependant effect of OXDC-CLEC therapy.

Example 14

Oral Oxalate Decarboxylase Therapy in Animal Model for Primary Hyperoxaluria

Mouse Model for Type I Primary Hyperoxaluria: AGT1 knockout mice lack the liver peroxisomal enzyme alanine: glyoxylate aminotransferase, a deficiency that causes primary hyperoxaluria, Type I. Chimeric mice were bred to homozygosity in C57B16 and 129/sv background strains. All homozygous Agxt mice showed mild hyperoxaluria (1-2 mmol/L), 5-10 fold urinary oxalate elevation over normal values, as compared to wildtype (0.2 mmol/L). It was also found that 30-50% of males, and 0% of females developed mild nephrocalcinosis and calcium oxalate calculi in the urinary tract later in life (4-7 months of age). Interestingly, when the mutation was analyzed in a homogeneous C57B16 strain, hyperoxaluria was not associated with development of urinary stones in either sex; underscoring the phenotypic variability typically observed in this disease.

A total of 44 male mice (strain AGT1 KO/129sv, developed by Dr. Salido, La Laguna Tenerife, Spain) were used in these experiments. Mice were randomly divided between a control group and three experimental groups. Mice weighed 20-25 grams and were less than 6 months of age.

The AGT1 KO (129 sv) mice were challenged with ethylene glycol (EG) to provoke severe hyperoxaluria and the formation of calcium oxalate deposits in the kidney parenchyma. EG is a common alcohol that is metabolized in the liver to oxalate. Usually, after 2-6 weeks of EG challenge, AGT1 KO mice in the 129/sv background show signs of impaired kidney function as determined by (i) the variable excretion of oxalate in the urine, (ii) decreased creatinine clearance, and (iii) nephrocalcinosis that ultimately leads to renal failure and death.

Mice were acclimated for 7 days prior to treatment to individual metabolic cages (Tecniplast USA Inc, Exton, Pa., USA), and were fed standard breeder diet (17% proteins, 11% fat, 53.5% carbohydrate) containing less than 0.02-0.08% oxalate and approximately 0.5-0.9% calcium. After the acclimation period, mice were divided into four groups; three treatment groups were fed oxalate decarboxylase-CLEC mixed with food, while mice in the matched control group received the same diet without addition of the test article. Drinking water supplemented with 0.7% EG was provided to all mice ad libitum from the first day of treatment until the end of the study. After several days of challenge, mice excrete approximately 3-6 mmol/L oxalate in their urine per day, which is approximately 10-20 fold more than wild type (unchallenged) mice.

Administration of OXDC-CLEC Enzyme; Dose Range Study: A total of 44 male mice from strain AGT1 KO/129 sv were used in a dose study of OXDC-CLEC. The mice weighed 20-25 grams and were less than 6 months of age. The mice were challenged with EG, and then were randomly divided between a control group and an experimental group. The efficacy of three different doses of recombinant oxalate decarboxylase, formulated as cross-linked crystals (1% glutaraldehyde; see Example 9), was monitored over four consecutive weeks. The term "OXDC-CLEC as used in this Example refers to recombinant oxalate decarboxylase, formulated as cross-linked crystals (1% glutaraldehyde, as described in Example 9. OXDC-CLEC was orally administered as a freeze/dried food enzyme mixture at nominal doses of 5, 25 and 80 mg/day. An adequate amount of enzyme slurry in 10 mM Tris-HCl buffer (pH 7.0) was mixed with 3.5 g food and freeze dried. Each morning, food containers were re-filled with ~7 g of the food/enzyme mixture.

Assessment of the efficacy of OXDC-CLEC: The efficacy of the enzyme therapy was monitored by urinary oxalate reduction, prevention of calcium oxa late deposition in kidney parenchyma, and survival. At the end of the study, surviving mice were sacrificed and blood samples taken for creatinine measurement.

Analysis of urine samples: 24 h urinary samples were collected in metabolic cages over acid (50 µl of 6 N hydrochloride acid per 3-4 ml of urine) in order to minimize the spontaneous breakdown of urinary ascorbic acid to oxalate. Urine samples were stored at −20° C. until further analysis. Daily diuresis and multiple 24 h urine samples were collected and analyzed for oxalate and creatinine levels. Assays for oxalate and creatinine are described in Example 15. Urinary excretion of oxalate and creatinine was expressed as µmol of oxalate or creatinine excreted in 24 h urine sample (mL). Data were analyzed statistically using Student's t-test.

Analysis of blood samples: At the end of the study, mice were sacrificed and serum samples were collected. For serum creatinine measurement, a slightly modified version of the Jaffe reaction method (see, e.g., the Creatinine Microassay Plate Kit from Oxford Medical Research, Inc.; Slot, *Scand J. Clin. Lab. Invest.* 17:381, 1965; and Heinegard D, Clin. Chim. Acta 43:305, 1973) was used. 80 µl of undiluted serum samples was mixed with 800 µl of picric alkaline in the cuvettes and incubated for 30 minutes at room temperature. Color development was measured spectrophotometrically at 510 nm; 33.3 µl of 60% acetic acid was then added to quench the unspecific reaction. Samples were thoroughly mixed and after 5 minutes incubation at room temperature were read again at 510 nm. Final absorbance is present as a difference of two readings. Serial dilutions of 1 mM creatinine solution was used for a standard curve.

Kidney function was monitored indirectly by measuring creatinine clearance. Creatinine clearance is expressed as excretion rate of creatinine ($U_{er} \times V$), where $U_{er}$ represents the concentration of creatinine (µmol/L) in a urine sample, divided by plasma creatinine ($P_{er}$). This is represented as:

$$C_{er} = (U_{er} \times V)/P_{er} = mL/h$$

The safety parameters monitored during the study were mortality, food and water intake, and body weight. Mortality checks and cage side clinical observations were performed once daily throughout the study. Food intake was measured daily and water intake was recorded weekly. Body weights of all animals were recorded at the beginning of the study and at the end of the study.

Figure 3:
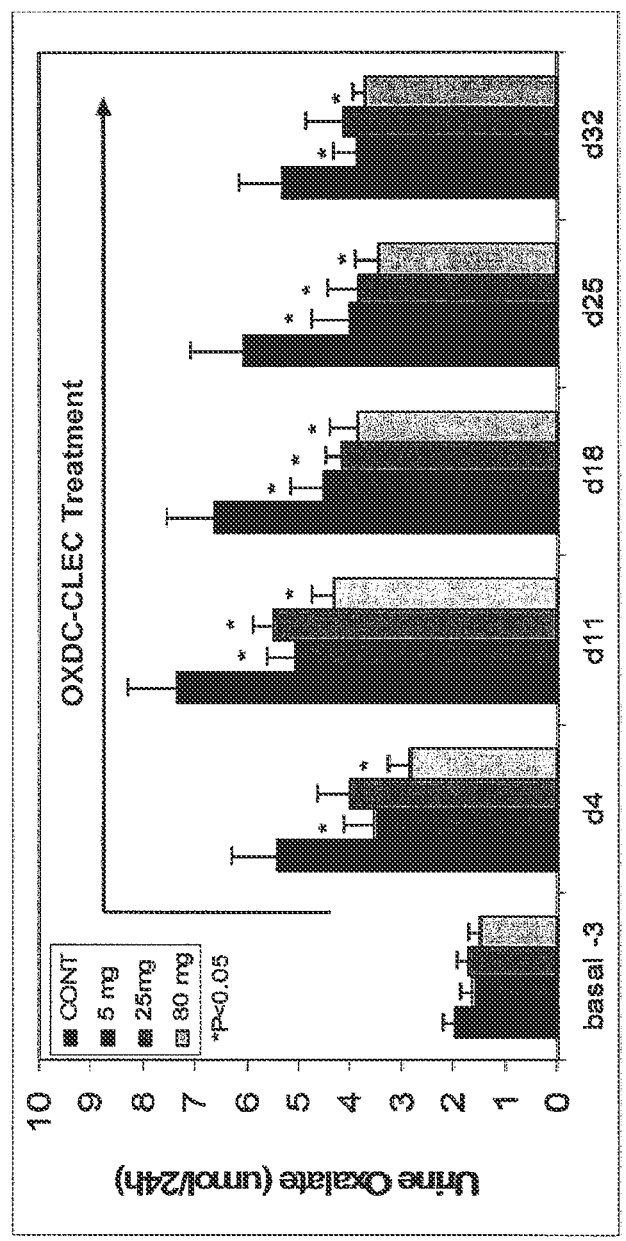
FIG. 3 is a bar graph depicting the effect of OXDC-CLEC on reduction of urinary oxalate levels in ethylene glycol-challenged AGT1 knock-out (KO) mice. Each bar represents the mean±SE. Asterisks indicate a significant difference between the control group and three treatment groups at p<0.05 at the time point, calculated using a two tailed Student's t-test.

As shown in FIG. 3, oral administration of OXDC-CLEC to EG-challenged AGT1 KO (129 sv) mice resulted in significant reduction of urinary oxalate levels from day 4 of the treatment until the end of the study when compared with matched untreated control mice. A reduction of between 30 and 50% was observed in all three treatment groups, with the maximal reduction observed in the highest dose group (80 mg of OXDC-CLEC). Lower doses of 25 mg and 5 mg of OXDC-CLEC produced reduction in urine oxalate up to 35%.

The results are analyzed by unpaired two tail Student's t-test. At the beginning of the study, each dosage group had n=1 mice, but several mice died during the course of the study due to the ethylene glycol challenge. The results presented include only mice that were alive at the particular day of urine oxalate measurements. The bell shaped curve of urinary oxalate excretion in the control group is best explained by the observation that initial elevation of urinary oxalate leads to nephrocalcinosis, reduced renal filtering function, and consequent lowered excretion rate of oxalate over time, and eventual death in the worst case.

Assessment of the renal function by creatinine clearance measurement. At the end of the study, all animals that survived 4 weeks of EG challenge were sacrificed and blood was collected to measure plasma creatinine and creatinine clearance. All 11 mice in the 80 mg dosage group survived the 4 weeks of EG challenge; 8 of 11 mice in the 25 mg OXCD-CLEC dosage group survived; 8 of 11 mice in the 5 mg OXCD-CLEC dosage group survived; and 7 of 11 mice in the control group survived. For serum creatinine measurement, the slightly modified Jaffe reaction method described above was used (see, e.g., the Creatinine Microassay Plate Kit from Oxford Medical Research, Inc.; Slot, *Scand J. Clin. Lab. Invest.* 17:381, 1965; and Heinegard, *Clin. Chim. Acta* 43:305, 1973).

Figure 4:
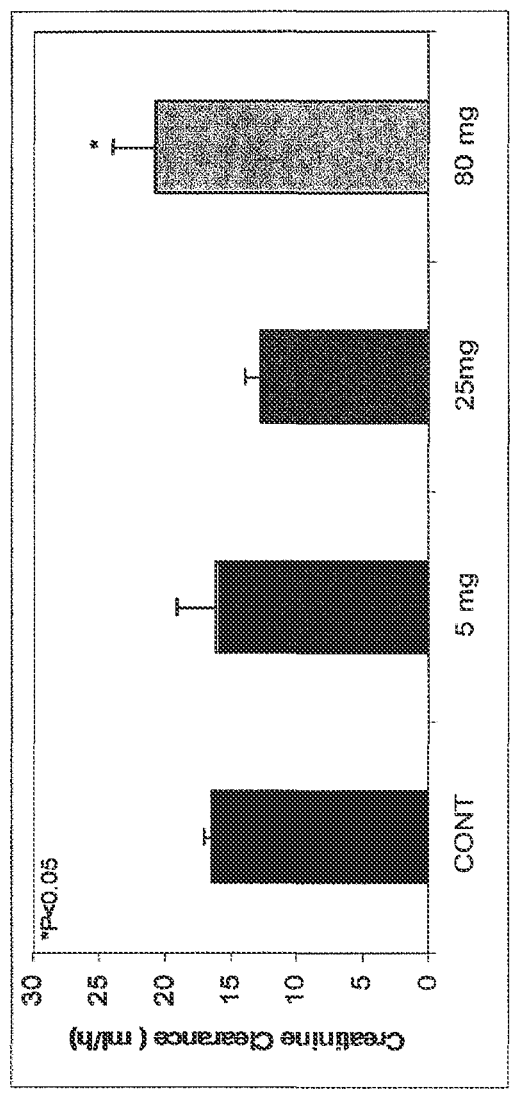
FIG. 4 is a bar graph depicting the effect of OXDC-CLEC on creatinine clearance in ethylene glycol-challenged AGT1 KO mice. Each bar represents the mean±SE. Asterisks indicate a significant difference between the control group and 80 mg treatment group at p<0.05 by a two tailed Student's t-test.

The efficacy of orally administered OXDC-CLEC on kidney function was assessed by measuring creatinine clearance. Creatinine clearance in the mice that survived the entire one month study period is shown in FIG. 4. When compared with the control group, creatinine clearance was significantly higher in surviving mice that received 80 mg of OXDC-CLEC ($p<0.05$).

All mice (11/11) in the 80 mg OXDC-CLEC treatment group survived the 4 week EG challenge regimen, while only 7 mice (7/11) in the control group survived the regimen. The kidney filtration rate, assayed by creatinine clearance, was also significantly lower than in the 80 mg dosage group (FIG. 4).

Kidney histopathology analysis: Mouse kidneys were routinely processed for paraffin embedding and positioned in order to obtain complete cross sections of the kidneys. Each kidney was cut in 12 serial sections at 4 µm per kidney and stained with either hemotoxylin and eosin for routine histological examination, or by specific Yasue metal substitution histochemical method to detect the presence of calcium oxalate crystals in the renal tissue. Slides were examined under the microscope using 20× magnification and examiner scored sections under 4-category scale, applying the same criteria to each of the anatomic areas in the kidney (cortex, medulla and papilla). The scoring was (i) none (no oxalate crystals in any field); (ii) minimal (1-5 crystals in any field); (iii) moderate (6-10 crystals in any field); and (iv) severe (all fields with multiple collections of crystals).

Figure 5:
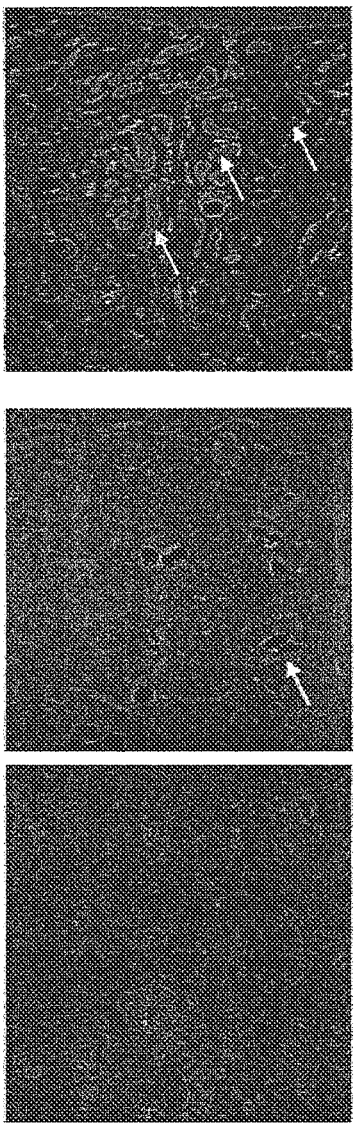
FIGS. 5A-5C are images showing the prevention of calcium oxalate deposits on kidney parenchyma following treatment with OXDC-CLEC.

Representative images of kidney tissue from both treatment and control animals are shown in FIGS. 5A-5C. Yasue-positive calcium oxalate crystals were visible in the kidney parenchyma at 20× magnification. All mice treated with 80 mg of OXDC-CLEC treatment group had normal healthy kidney with no traces of calcium oxalate deposits (FIG. 5A). Moderate nephrocalcinosis (FIG. 5B) and severe nephrocalcinosis (FIG. 5C) were observed in the control group and in some mice from low dose treatment groups. The white arrows indicate calcium oxalate deposits and the gray arrows in FIG. 5C indicate large area with interstitial fibrosis.

Histological examination of the kidneys using the specific Yasue metal substitution method showed deposits primarily in the cortex and medullar part of the kidneys. In the case of severe nephrocalcinosis (FIG. 5C), calcium oxalate deposits were randomly distributed in the kidneys. Signs of fibrosis and inflammation were also visible and the morphology of glomeruli was changed with the occasionally formation of calcium oxalate deposits within the glomeruli. All mice (11/11) from the 80 mg dosage group had normal morphology of the kidneys upon necropsy with no traces of calcium oxalate deposition either in the kidney or in the urinary bladder. In contrast, 100% (11/11) of mice from untreated control group had calcium oxalate deposits. In the low treatment groups (25 mg or 5 mg of OXDC-CLEC), 63% (7/11) of mice had calcium oxalate deposits in the kidneys. These results demonstrate a positive, dose dependent effect of the oral therapy with OXDC-CLEC in the EG-challenged AGT1 KO mice on the reduction of hyperoxaluria and the prevention of calcium oxalate crystal deposition in the kidneys. A summary of the histopathological analysis from all 4 groups of mice is presented in Table 3.

TABLE 3

Severity of Nephrocalcinosis and Number of Mice Affected in Treated and Control Group Following Oral OXDC-CLEC Treatment.

NUMBER OF MICE WITH NEPHROCALCINOSIS

| DOSE GROUPS* | SEVERE | MODERATE | MINIMAL | NONE | CALCIUM OXALATE DEPOSITS (%) |
|---|---|---|---|---|---|
| CONT n = 11 | 4 (4 died) | — | 7 | — | 100 |
| 80 mg n = 11 | — | — | — | 11 | 0 |
| 25 mg n = 11 | 3 (3 died) | 2 | 2 | 4 | 63 |
| 5 mg n = 11 | 3 (3 died) | — | 4 | 4 | 63 |

The efficacy of the oral OXDC-CLEC treatment on the frequency of urinary stone formation in control mice and mice from three different treatment groups was also evaluated. Two main types of calculi were found in the urinary bladder from EG AGT1 KO mice: calcium oxalate monohydrate stones and calcium oxalate dihydrate stones. Grossly visible bladder stones were present in 36% (4/11) of the mice in the control group and in 19% (2/11) of the mice in the two lower treatment groups. No bladder stones were observed in the 80 mg high dose OXDC-CLEC group. The X-ray diffraction analysis showed that stones with whitish, rough budding surface are mostly composed of calcium oxalate monohydrate, while relatively large stones with sharp crystal angles correspond to calcium oxalate dihydrate.

Figure 6:
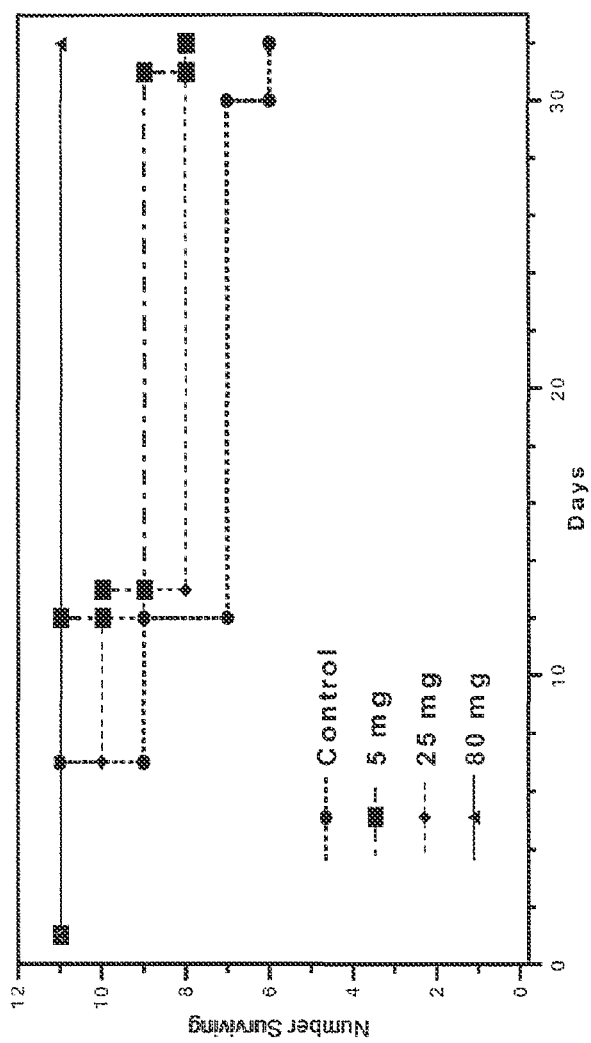
FIG. 6 is a Kaplan-Meier survival plot comparing the survival times of EG-challenged mice treated with three different doses of OXDC-CLEC or a vehicle control.

Survival rate analysis by Kaplan-Meier estimator. The effect of OXDC-CLEC treatment on survival rate of mice challenged with ethylene glycol was analyzed using the Kaplan-Meier method where survival of subjects that died in the certain time point is divided by the number of subjects who were still in the study at the time. This method graphically illustrates the difference between the groups in the study (FIG. 6). Often statistical programs such as Kaleida graph and STATS are used for calculations.

Oral treatment with OXDC-CLEC increased the survival rate of EG-challenged AGT1 KO mice as compared to that of the matched controls. All mice (11/11) from the 80 mg OXDC-CLEC treatment group survived the 30 day study period without signs of sickness, while 4 of 11 mice from the control group had severe nephrocalcinosis with development of urinary stones.

Since OXDC-CLEC is intended for oral administration, the potential for adverse reactions of the crosslinked crystals on gastrointestinal (GI) tissues was evaluated. The digestive tracts of treated EG-challenged AGT1 KO mice were examined macroscopically, and histological analysis with a hemotoxylin-eosin stain was performed on different parts of the GI tract including the stomach (corpus and antrum) and small bowel (jejunum and ileum). The evaluation confirmed that four weeks of oral treatment with OXDC-CLEC was well-tolerated and did not cause structural or morphological changes in the GI tract. Similar results were observed for the large bowel.

Summary of the Dose Range Study in EG-Challenged AGT1 KO Mice Orally Treated with Oxalate Decarboxylase-CLEC. Oral treatment with OXDC-CLEC in a primary hyperoxaluria animal model was safe and efficacious. In summary, four weeks of oral treatment with OXDC-CLEC reduced urinary oxalate by 30-50%. Significant and sustained reduction was recorded with each of the three doses of the test article evaluated. Four weeks of oral treatment prevented calcium oxalate deposition in the kidney parenchyma at the highest treatment dose. Four weeks of oral treatment increased the survival rate at the two lower doses and prevented animal mortality at the highest dose studied. Finally, the 4 week treatment regimen, did not produce macroscopic or microscopic changes in the GI tract.

Example 15

Assays

Protein Concentration Determination: The concentration of oxalate decarboxylase was determined by measuring absorbance at 280 nm. The absorbance of 1.36 optical density (OD) was considered as 1 mg/ml.

OXDC Activity Assay: The modified Sigma Aldrich protocol (Enzymatic Assay of Oxalate Decarboxylase EC 4.1.1.2) was used to measure the activity of soluble oxalate decarboxylase, oxalate decarboxylase crystals, and cross-linked oxalate decarboxylase crystals (OXDC-CLEC). This is an indirect two-step activity assay; in the first reaction OXDC converts the substrate oxalate to formate and carbon dioxide. In the second reaction, formate hydrogen is stoichiometrically transferred to NAD to form NADH by formate dehydrogenase. The ensuing concentration of NADH is quantified spectrophotomerically at 340 nm. Unit (u) of enzymatic activity is defined as follows: one Unit of oxalate decarboxylase will form 1.0 µmol of oxalate to formate and carbon dioxide per minute at pH 5 and 37° C.

Assay samples were normalized at a concentration of 0.007-0.02 and 0.009-0.03 mg/mL for OXDC crystals and OXDC-CLEC, respectively, in 5 mM potassium phosphate buffer pH 7.0 with 1 mM DTT (Sigma). Protein concentrations were determined by absorbance at 280 nm. Formate dehydrogenase (FDH) at 40 U/mL was prepared in cold diH$_2$O prior to use and kept on ice. All other reagents were kept at room temperature. Reagents were added to 2 ml microtubes with stir bar in the following order: 300 µL of 100 mM potassium phosphate and 200 µL of potassium oxalate pH 4.0 were mixed and warmed for 5 min in a water bath at 37° C., then 100 µL of 5 mM potassium phosphate with 1 mM DTT was added to the blank vial and 100 µL of diluted oxalate decarboxylase was added to all other vials. After 2 minutes, the reaction was stopped with 150 mM potassium phosphate dibasic. In the second reaction, 25 µL of NAD solution was added to 100 µL of FDH solution, and the incubation was continued for another 20 min. All samples were then centrifuged for 1 min at 16,100 rpm. Reaction mixtures were then transferred to 1.5 mL UV cuvettes, and absorbance at 340 nm was determined and recorded using a Shimadzu BioSpec (Shimadzu Scientific Instruments, Columbia, Md.).

Enzyme specific activity was calculated as follows:

$$\text{Units/mL } OXDC = \frac{[Abs \times \text{Total volume}(1.725 \text{ mL}) \times dil.\text{ factor}]}{(Ext.\ NADH = 6.22)(Vol.\ OXDC = 0.1 \text{ mL})}$$

(assay time = 2/5 min)

In a specific experiment, cross-linked crystals of oxalate decarboxylase (OXDC-CLEC) (diamond shaped crystals cross-linked with 1% glutaraldehyde by tumbling overnight; see Example 9) were compared to OXDC crystals. OXDC-CLEC retained 50% of the activity of the corresponding crystalline OXDC preparation.

Oxalate determination by colorimetric method: Oxalate colorimetric kit for quantitative determination of oxalate in the urine were purchased from Trinity Biotech USA (St. Louis, Mo.) or Greiner Diagnostic AG (Dennliweg 9, Switzerland). The urine samples were diluted and treated according to the manufacturer's instruction. The assay comprises two enzymatic reactions: (a) oxalate is oxidized to carbon dioxide and hydrogen peroxide by oxalate oxidase, and (b) the hydrogen peroxide thus formed reacts with 3-methyl-2-benzothiazolinone hydrazone (MBTH) and 3-(dimethylamino)benzoic acid (DMAB) in the presence of peroxidase to yield an indamine dye which can be detected by absorbance at 590 nm. The intensity of the color produced is directly proportional to the concentration of oxalate in the sample. Urine oxalate values are calculated from standard curve.

Creatinine determination by colorimetric method: Creatinine colorimetric kits for the quantitative determination of creatinine in the urine were purchased from Quidel Corporation (San Diego, Calif.; METRA Creatinine Assay kit) or Randox Laboratories (Antrim, United Kingdom). The assay is based on the principle that creatinine reacts with picric acid in alkaline solution to form a product that has an absorbance at 492 nm. The amount of complex formed is directly proportional to the creatinine concentration. 24 h rat urine samples collected from single metabolic cages were diluted 15 fold with double distilled water. 20 µl of diluted urine sample was mixed with 20 µl picric acid/sodium hydroxide (1:1). Absorbance at 492 nm was measured after incubating for 2 minutes incubation at room temperature. Urinary creatinine values were calculated from standard curve.

Example 16

OXDC Therapy for the Treatment of Oxalate-Associated Disorders in Humans

Humans in need of treatment or prevention of an oxalate-associated disorder such as hyperoxaluria can be treated by oral administration of cross-linked oxalate decarboxylase crystals. The oxalate decarboxylase crystals are administered at an approximate dose of 10 µg/kg to 25 mg/kg; 1 mg/kg to 25 mg/kg, or 5 mg/kg to 100 mg/kg, as determined by a treating clinician and depending on the severity of the symptoms and the progression of the disease. The oxalate decarboxylase crosslinked crystals are administered 1, 2, 3, 4, or 5 times daily, or are administered less frequently, such as once or twice a week. This oral administration of OXDC-CLEC results in a decrease in urinary oxalate levels of at least 10%, 20%, 25%, 30%, 35%, 40%, 45%, 50%, 55%, 60%, 70% or more.

Example 17

Recombinant Production of Oxalate Decarboxylase

In Human Embryonic Kidney (HEK293) cells: DNA encoding OXDC (e.g., SEQ ID NO: 1 or 2) is cloned into a suitable expression vector. After sequence confirmation, the vector can be linearized and transformation of the linearized vector to pre-seeded HEK293 cells may be carried out using Lipofectamine™ 2000 Transfection Reagent in a 6 cm diameter dish. The transfection reaction is cultured overnight in appropriate medium, and then transformants are selected in medium supplemented with 0.5 g/L of neomycin. Stably transfected HEK293 cell clones are identified after growth in neomycin-containing medium for up to 3 weeks. The clones are then isolated and propagated, and used for OXDC expression.

In Chinese Hamster Ovary (CHO) cells: DNA encoding OXDC gene is cloned into a suitable expression vector. Cultured CHO lec 3.2.8.1 cells are then detached by trypsin digestion and harvested by centrifugation. The cells are then suspended in Electroporation phosphate buffered saline buffer (EPBS) to a final concentration of ~1×10$^7$/ml, and transformed with the linearized vector by electroporation. After overnight culture, the medium is exchanged with medium supplemented with 0.5 g/L neomycin. Successive changes of medium are performed to screen for stably transfected CHO cell clones. Once the stably transfected cell clones are established and propagated, the cells are used for OXDC expression.

In *Pichia Pastoris*: DNA encoding the OXDC gene is cloned into a suitable expression vector. After sequence confirmation, the vector can be linearized then transformed into a *Pichia Pastoris* host cell (see, Whittaker et al., *J. Biol. Inorg. Chem.* 7:136-145, 2002). Transformants are selected with Zeocin, expanded in buffered glycerol complex medium (BMGY), and induced with methanol. OXDC may then be isolated from the culture medium.

In *Saccharomyces cerevisiae*: The synthetic OXDC gene can be cloned into a suitable expression vector containing, for example, the Gal1 promoter (pGal) and terminator sequences for expression. After sequence confirmation, the expression vector is transformed into the competent *Saccharomyces cerevisiae* W303-1A by electroporation. The transformants are screened and propagated before use for OXDC expression.

In insect cells: DNA encoding OXDC may be cloned into a suitable expression vector, such as, e.g., a baculovirus system. After sequence confirmation, the vector may be transformed into competent DH10Bac *E. coli* cells, and *E. coli* cells containing the recombinant bacmid can be screened and verified. The recombinant bacmid DNA is isolated and used to transfect insect Sf9 cells using reagents such as Cellfectin™ reagent (Invitrogen, Carlsbad, Calif.). The recombinant baculovirus particles can then be isolated, propagated, and titered before use to infect Sf9 cells for OXDC expression.

In *E. Coli*: DNA encoding OXDC is cloned into a suitable *E. coli* expression vector. After sequence confirmation, the vector is transformed into competent *E. coli* BL21 or if necessary *E. coli* Origami B (DE3), which allows the formation of disulfide bonds in the recombinant protein expressed in this strain. The transformants are screened by growing the transformants on nutrient plates containing antibiotics and verified by colony PCR using OXDC gene specific primers. The transformants are then cultured in the liquid medium and induced with isopropyl-beta-D-thiogalactopyranoside (IPTG) for OXDC expression.

Example 18

Sequences

*Collybia velutipes* sequence (SEQ ID NO:1) to express in *Candida boidinii*. Two Not 1sequences are underlined; the ATA triplet in bold is a spacer codon; the double-underlined sequence is alpha mating factor sequence optimized for *C. Boidinii*; the OXDC coding sequence is depicted in lower-case letters.

1    ataagaatGCGGCCATAATGATTTCCATCTATTTTTACTGCTGTT
50   TTATTTGCTGCTTCTTCTGCTTTAGCTGCTCCAGTTAATACTACTACTGA
100  AGATGAAACTGCTCAAATTCCAGCTGAAGCTGTTATTGGTTATTCTGATT
150  TAGAAGGTGATTTTGATGTTGCTGTTTTACCATTTTCTAATTCTACTAAT
200  AATGGTTTATTATTTATTAATACTACTATTGCTTCTATTGCTGCTAAAGA
250  AGAAGGTGTTTCTTTAGAAAAAAGAGAAGCTGAAGCTatgtttaataatt
300  ttcaaagattattaactgttattttattatctggttttactgctggtgtt
350  ccattagcttctactactactggtactggtactgctactggtacttctac
400  tgctgctgaaccatctgctactgttccatttgcttctactgatccaaatc
450  cagttttatggaatgaaacttctgatccagctttagttaaaccagaaaga
500  aatcaattaggtgctactattcaaggtccagataatttaccaattgattt
550  acaaaatccagatttattagctccaccaactactgatcatggttttgttg
600  gtaatgctaaatggccattttcttttctaaacaaagattacaaatggt
650  ggttgggctagacaacaaaatgaagttgttttaccattagctactaattt
700  agcttgtactaatatgagattagaagctggtgctattagagaattacatt
750  ggcataaaaatgctgaatgggcttatgttttaaaagggtctactcaaatt
800  tctgctgttgataatgaagggagaaattatatttctactgttggtccagg
850  tgatttatggtattttccaccaggtattccattctttacaagctactg
900  ctgatgatccagaaggttctgaatttattttagttttgattctggtgct
950  tttaatgatgatggtactttttttattaactgattggttatctcatgttcc
1000 aatggaagttattttaaaaaatttagagctaaaaatccagctcttggt
1050 ctcatattccagctcaacaattatatattttccatctgaaccaccagct
1100 gataatcaaccagatccagtttctccacaagggactgttccattaccata
1150 ttcttttaattttttcttctgttgaaccaactcaatattctggtgggactg
1200 ctaaaattgctgattctactacttttaatatttctgttgctattgctgtt
1250 gctgaagttactgttgaaccaggtgctttaagagaattacattggcatcc
1300 aactgaagatgaatggacttttttttatttctggtaatgctagagttacta
1350 tttttgctgctcaatctgttgcttctacttttgattatcaaggtggtgat
1400 attgcttatgttccagcttctatgggtcattatgttgaaaatattggtaa
1450 tactactttaacttatttagaagttttttaatactgatagatttgctgatg
1500 tttctttatctcaatggttagctttaactccaccatctgttgttcaagct
1550 catttaaatttagatgatgaaactttagctgaattaaaacaatttgctac
1600 taaagctactgttgttggtccagttaattaaGCGGCCGCtaaactat 1646

*Bacillus subtilis* sequence (SEQ ID NO:2): The underlined "G" at position 705 indicates an A→G base substitution. This base substitution does not alter the amino acid sequence.

1    ATGAAAAAACAAAATGACATTCCGCAGCCAATTAGAGGAGACAAAGGAG
50   CAACGGTAAAAATCCCGCGCAATATTGAAAGAGACCGGCAAAACCCTGAT
100  ATGCTCGTTCCGCCTGAAACCGATCATGGCACCGTCAGCAATATGAAGTT
150  TTCATTCTCTGATACTCATAACCGATTAGAAAAAGGCGGATATGCCCGGG

-continued

```
 200  AAGTGACAGTACGTGAATTGCCGATTTCAGAAAACCTTGCATCCGTAAAT
 250  ATGCGGCTGAAGCCAGGCGCGATTCGCGAGCTTCACTGGCATAAAGAAGC
 300  TGAATGGGCTTATATGATTTACGGAAGTGCAAGAGTCACAATTGTAGATG
 350  AAAAAGGGCGCAGCTTTATTGACGATGTAGGTGAAGGAGACCTTTGGTAC
 400  TTCCCGTCAGGCCTGCCGCACTCCATCCAAGCGCTGGAGGAGGGAGCTGA
 450  GTTCCTGCTCGTGTTTGACGATGGATCATTCTCTGAAAACAGCACGTTCC
 500  AGCTGACAGATTGGCTGGCCCACACTCCAAAAGAAGTCATTGCTGCGAAC
 550  TTCGGCGTGACAAAAGAAGAGATTTCCAATTTGCCTGGCAAAGAAAAATA
 600  TATATTTGAAAACCAACTTCCTGGCAGTTTAAAAGATGATATTGTGGAAG
 650  GGCCGAATGGCGAAGTGCCTTATCCATTTACTTACCGCCTTCTTGAACAA
 700  GAGCCGATCGAATCTGAGGGAGGAAAAGTATACATTGCAGATTCGACAAA
 750  CTTCAAAGTGTCTAAAACCATCGCATCAGCGCTCGTAACAGTAGAACCCG
 800  GCGCCATGAGAGAACTGCACTGGCACCCGAATACCCACGAATGGCAATAC
 850  TACATCTCCGGTAAAGCTAGAATGACCGTTTTTGCATCTGACGGCCATGC
 900  CAGAACGTTTAATTACCAAGCCGGTGATGTCGGATATGTACCATTTGCAA
 950  TGGGTCATTACGTTGAAAACATCGGGGATGAACCGCTTGTCTTTTTAGAA
1000  ATCTTCAAAGACGACCATTATGCTGATGTATCTTTAAACCAATGGCTTGC
1050  CATGCTTCCTGAAACATTTGTTCAAGCGCACCTTGACTTGGGCAAAGACT
1100  TTACTGATGTGCTTTCAAAAGAAAAGCACCCAGTAGTGAAAAAGAAATGC
1150  AGTAAATAA                                        1158
```

The translated oxalate decarboxylase protein from *Bacillus subtilis* sequence is shown below (Swiss-Prot: O34714) (SEQ ID NO:3).

```
  1  MKKQNDIPQPIRGDKGATVKIPRNIERDRQNPDMLVPPETDHGTVSNMK
 50  FSFSDTHNRLEKGGYAREVTVRELPISENLASVNMPLKPGAIRELHWHKE
100  AEWAYMIYGSARVTIVDEKGRSFIDDVGEGDLWYFPSGLPHSIQALEEGA
150  EFLLVFDDGSFSENSTFQLTDWLAHTPKEVIAANFGVTKEEISNLPGKEK
200  YIFENQLPGSLKDDIVEGPNGEVPYPFTYRLLEQEPIESEGGKVYIADST
250  NFKVSKTIASALVTVEPGAMRELHWHPNTHEWQYYISGKARMTVFASDGH
300  ARTFNYQAGDVGYVPFAMGHYVENIGDEPLVFLEIFKDDHYADVSLNQWL
350  AMLPETFVQAHLDLGKDFTDVLSKEKHPVVKKKCSK            385
```

Example 19

Stability of Soluble OXDC, Crystalline OXDC and OXDC-CLEC at Low pH 3.0

Figure 7:
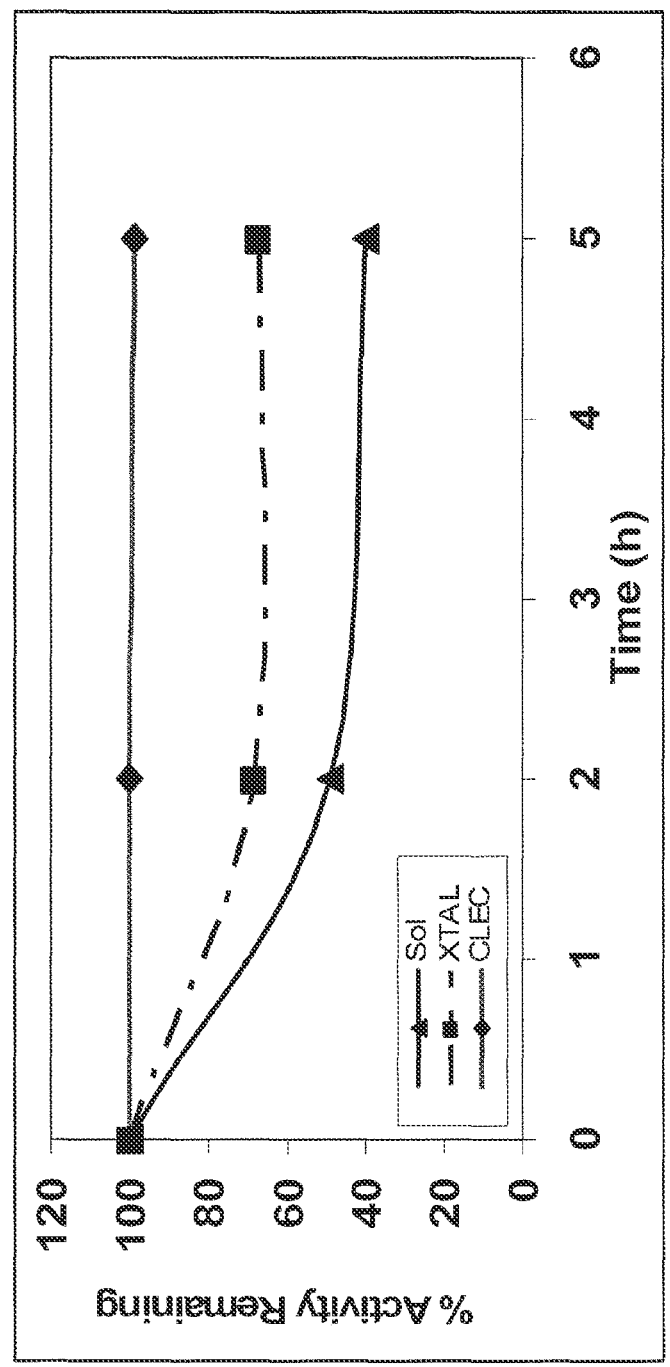
FIG. 7 is a graph depicting the stability of soluble oxalate decarboxylase ("Sol"), oxalate decarboxylase crystals ("XTAL"), and cross-linked oxalate decarboxylase crystals ("CLEC") at low pH at the time intervals indicated.

Soluble OXDC, 2.5 mg/mL (Example 5), crystalline OXDC, 5.0 mg/mL (Example 5) and OXDC-CLEC, 5.0 mg/mL (Example 10) were taken in sodium citrate buffer pH 3.0, 1 mL each in eppendorf tubes and incubated for 5 h at 37° C. Samples were taken at 0, 2 and 5 hrs for measurement of stability of the enzyme. The activities were determined as in Example 15. Results showing the stability of OXDC and OXDC-CLEC at pH 3.0 after 0, 2, and 5 hrs are shown in FIG. 7. OXDC-CLEC retained about 100% activity after 5 h of incubation at pH 3.0, while soluble OXDC within first 2 h lost about 51% activity and after 5 h had only about 40% activity remained when compared with original. The crystalline OXDC was more stable than the soluble OXDC by retaining about 68% activity in 1 hr and about 67% activity in 2 hr.

Example 20

Stability of Soluble OXDC, Crystalline OXDC, and OXDC-CLEC Crystals in the Presence of Pepsin Soluble OXDC, 1.0 mg/mL (Example 5), crystalline OXDC, 10.0 mg/mL (Example 5) and OXDC-CLEC, 1.0 mg/mL (Example 10) were taken in sodium citrate buffer pH 3.0, 1 mL each in eppendorf tubes and incubated with pepsin (pepsin stock was made at a concentration of 1 mg/mL in 25 mM Tris-HCL buffer, pH 7.5) at a ratio of 50:1 between OXDC to pepsin for 5 h at 37° C. Samples were taken at 0, 2 and 5 hrs for measurement of stability of the enzyme. The activities were determined as in Example 15. Results showing the stability of soluble OXDC, crystalline OXDC and OXDC-CLEC in the presence of pepsin after 0, 2, and 5 hrs are depicted in FIG. 8.

Figure 8:
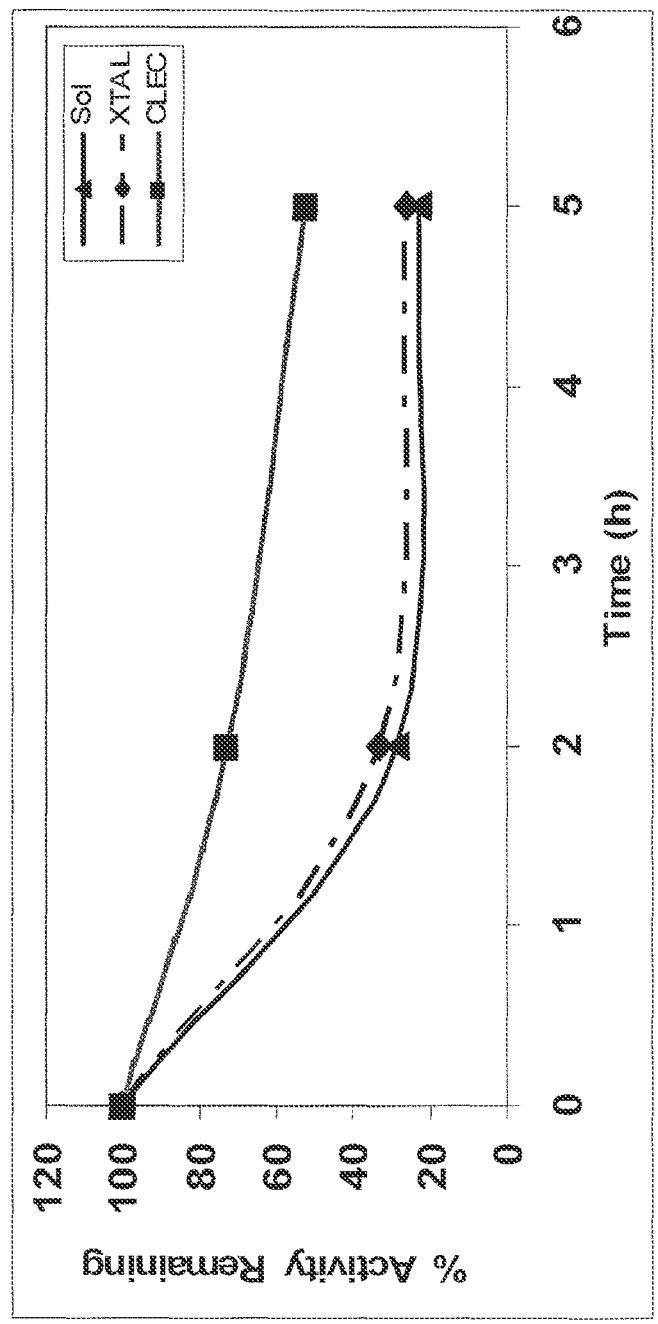
FIG. 8 is a graph depicting the stability of soluble oxalate decarboxylase ("Sol"), oxalate decarboxylase crystals ("XTAL"), and cross-linked oxalate decarboxylase crystals ("CLEC") in the presence of pepsin at pH 3.0 at the time intervals indicated.

As shown in FIG. 8, superiority of the OXDC-CLEC formulation versus soluble OXDC was revealed at both low pH and in the presence of pepsin. OXDC-CLEC sample retained about 60% activity after 5 h incubation at 37° C., while majority of soluble OXDC and uncrosslinked crystalline OXDC were degraded after 2 h by pepsin and only about 20% activity remained after 5 h.

Example 21

Stability of Soluble OXDC, Crystalline OXDC, and OXDC-CLEC in the Presence of Chymotrypsin Soluble OXDC, 1.0 mg/mL (Example 5), crystalline OXDC, 10.0 mg/mL (Example 5) and OXDC-CLEC, 1.0 mg/mL (Example 10) were taken in 25 mM Tris-HCl buffer at pH 7.5, 1 mL each in eppendorf tubes and incubated with chymotrypsin (chymotrypsin stock was made at a concentration of 1 mg/mL in 25 mM Tris-HCl buffer, pH 7.5, freshly prepared) at a ratio of 50:1 between OXDC to chymotrypsin for 5 h at 37° C. Samples were taken at 0, 2 and 5 hours for measurement of stability of the enzyme. The activities were determined as in Example 15. Results showing the stability of soluble OXDC, crystalline OXDC and OXDC-CLEC in the presence of chymotrypsin at 0, 2 and 5 hours are shown in FIG. 9.

Figure 9:
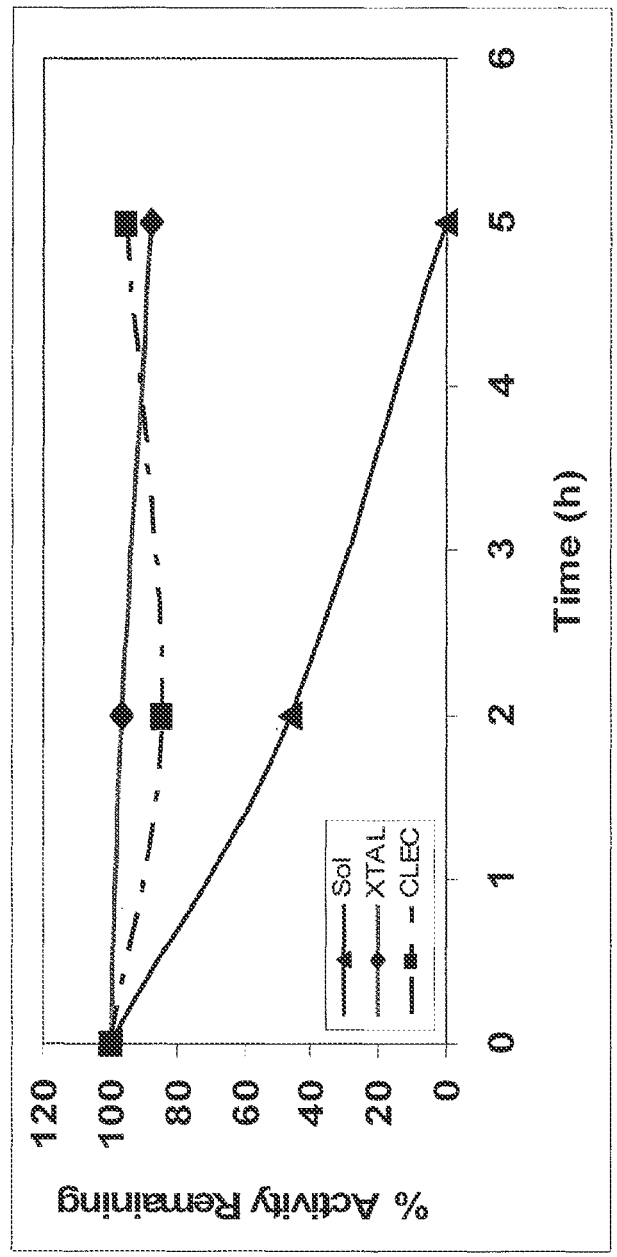
FIG. 9 is a graph depicting the stability of soluble oxalate decarboxylase ("Sol"), oxalate decarboxylase crystals ("XTAL"), and cross-linked oxalate decarboxylase crystals ("CLEC") in the presence of chymotrypsin at pH 7.5 at the time intervals indicated.

Results from FIG. 9 show that OXDC-CLEC and uncrosslinked crystalline OXDC were stable and resistant to proteolytic cleavage by chymotrypsin after 5 hours of incubation at 37° C. Analysis showed that OXDC-CLEC and uncrosslinked crystalline OXDC enzyme retained about 100% activity when compared to its original values in 5 hours. At the same time, soluble protein lost about 50% activity after 2 hours exposure to chymotrypsin and 5 hours later all soluble OXDC was degraded, with 0% activity remained.

Example 22

Stability of Soluble OXDC, Crystalline OXDC, and OXDC-CLEC in the Simulated Intestinal Juice with Pancreatin Soluble OXDC, 5.0 mg/mL (Example 5), crystalline OXDC, 10.0 mg/mL (Example 5) and OXDC-CLEC, 10.0 mg/mL (Example 10) were taken in simulated intestinal juice (simulated intestinal juice made according to USB recommendation. 6.8 gm of monobasic potassium phosphate was dissolved in 250 ml of water, mixed with 77 ml 0.2 N of sodium hydroxide and 500 ml of deionized water; then, 10 gm of pancreatin was added and pH was adjusted with either 0.2N hydrochloric acid or 0.2 N sodium hydroxide to a pH of 6.8; water was added to 1 L), 1 mL each, in eppendorf tubes and incubated for 2 h at 37° C. Samples were taken at 0, 1 and 2 hrs for measurement of stability of the enzyme. The activities were determined as in Example 15. The results are shown in FIG. 10.

Figure 10:
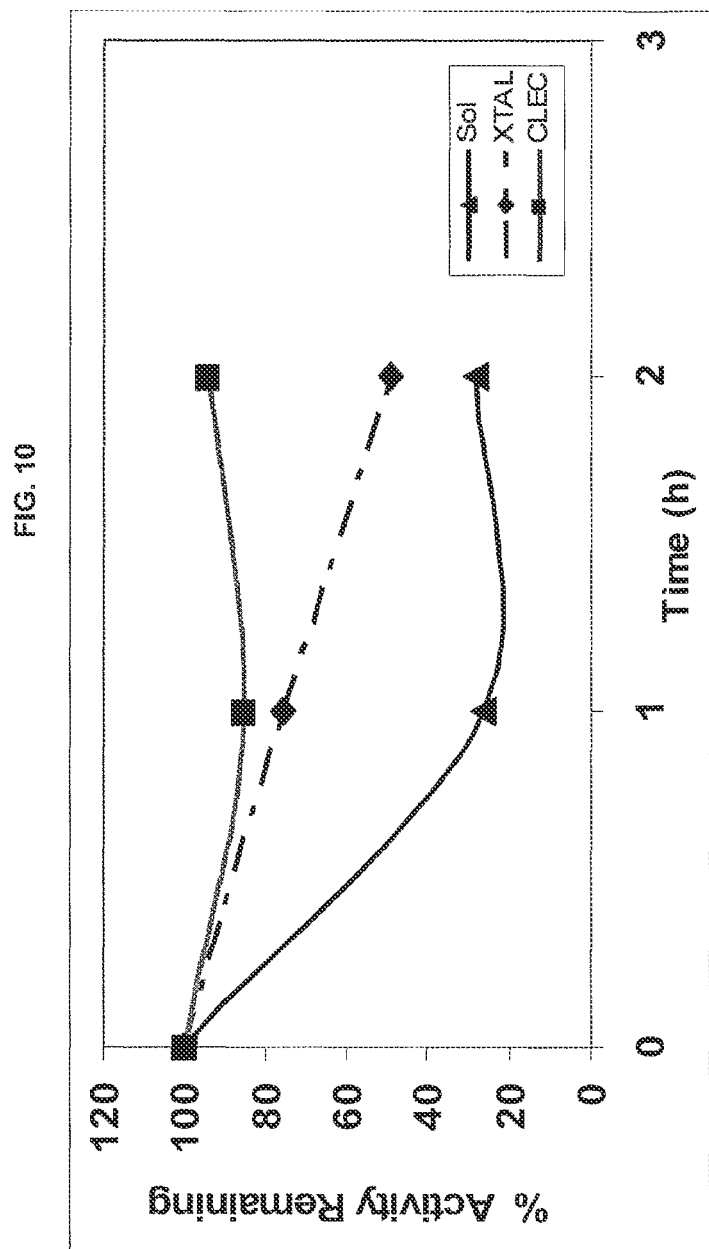
FIG. 10 is a graph depicting the stability of soluble oxalate decarboxylase ("Sol"), oxalate decarboxylase crystals ("XTAL"), and cross-linked oxalate decarboxylase crystals ("CLEC") in the presence of simulated intestinal juice with pancreatin at pH 6.8 at the time intervals indicated.

The results, shown in FIG. 10 indicate that OXDC-CLEC is stable in simulated intestinal juice with pancreatin with about 100% activity preserved. In contrast, the majority of soluble OXDC was degraded by pancreatin (mix of lipase, amylase and protease) within 1 hour and only between about 26%-28% activity remained after 1 h and 2 h incubation, respectively. The uncrosslinked crystalline OXDC was much more stable than its soluble form in the presence of pancreatin where it lost only about 76% and about 49% activities after 1 and 2 hr incubation, respectively.

In addition, OXDC-CLEC protects the enzyme from cleavage from proteases, such as pepsin and chymotrypsin. Stability of OXDC-CLEC can be at least about 100%, 200%, 300%, 400% or more of that of the stability of soluble OXDC in the same conditions. OXDC-CLEC maintains its activities at least about 2, 3, or 4 folds higher than soluble OXDC maintaining its activities under the same conditions. Thus, compared to soluble OXDC, OXDC-CLEC is both active and stable in the severe conditions of the gut, ranging from acidic pH of about 2.5 or 3 to pH of about 7.5 or 8.5 and containing various proteases.

A number of embodiments of the invention have been described. Nevertheless, it will be understood that various modifications may be made without departing from the spirit and scope of the invention. Accordingly, other embodiments are within the scope of the following claims.

What is claimed is:

1. A pharmaceutical composition comprising spray-dried biologically active oxalate decarboxylase crystals having a moisture content of less than 5% by weight, wherein the oxalate decarboxylase is uncrosslinked and is capable of converting oxalate to formate.

2. The pharmaceutical composition of claim 1, wherein the oxalate decarboxylase crystals are about 1 μm to about 25 μm in length.

3. The pharmaceutical composition of claim 1, further comprising at least one excipient selected from a sugar, sugar alcohol, viscosity increasing agent, wetting agent, solubilizing agent, buffer salt, emulsifying agent, antimicrobial agent, and an antioxidant.

4. The pharmaceutical composition of claim 1, wherein the composition is an oral dosage form.

5. The pharmaceutical composition of claim 4, wherein the oral dosage form is formulated as a capsule.

6. The pharmaceutical composition of claim 4, wherein the oral dosage form is formulated as a tablet.

7. The pharmaceutical composition of claim 1, wherein the oxalate decarboxylase retains at least 50% of its activity upon exposure to an aqueous solution having a pH of about 6.8 for 1 hour.

8. The pharmaceutical composition of claim 1, wherein the oxalate decarboxylase is a recombinant oxalate decarboxylase.

9. The pharmaceutical composition of claim 1, wherein the oxalate decarboxylase has an amino acid sequence which has at least 95% sequence identity with SEQ ID NO: 3.

* * * * *